US012605367B2

(12) United States Patent
Pietropaolo et al.

(10) Patent No.: US 12,605,367 B2
(45) Date of Patent: Apr. 21, 2026

(54) METHODS OF TREATMENT AND/OR PREVENTION OF DISORDERS AND SYMPTOMS RELATED TO BKCa AND/OR SK CHANNELOPHATHIES

(71) Applicants: UNIVERSITE DE BORDEAUX, Bordeaux (FR); ASSETSUP, Rueil-Malmaison (FR); CENTRE NATIONAL DE LA RECHERCHE SCIENTIFIQUE, Paris (FR)

(72) Inventors: Susanna Pietropaolo, Bordeaux (FR); Wilhelmus Crusio, Pompignac (FR); Valérie Lemaire, Birac (FR); Eric Louette, Rueil-Malmaison (FR)

( * ) Notice: Subject to any disclaimer, the term of this patent is extended or adjusted under 35 U.S.C. 154(b) by 977 days.

(21) Appl. No.: 17/760,612

(22) PCT Filed: Sep. 15, 2020

(86) PCT No.: PCT/EP2020/075754
§ 371 (c)(1),
(2) Date: Mar. 15, 2022

(87) PCT Pub. No.: WO2021/052952
PCT Pub. Date: Mar. 25, 2021

(65) Prior Publication Data
US 2022/0313664 A1 Oct. 6, 2022

(30) Foreign Application Priority Data

Sep. 16, 2019 (EP) .................................... 19197502

(51) Int. Cl.
| A61K 31/423 | (2006.01) |
| A61K 31/135 | (2006.01) |
| A61K 31/185 | (2006.01) |
| A61K 31/366 | (2006.01) |
| A61K 31/40 | (2006.01) |
| A61K 31/403 | (2006.01) |
| A61K 31/4168 | (2006.01) |
| A61K 31/437 | (2006.01) |
| A61K 31/4425 | (2006.01) |
| A61K 31/573 | (2006.01) |
| A61K 31/65 | (2006.01) |
| A61P 25/28 | (2006.01) |

(52) U.S. Cl.
CPC .......... *A61K 31/423* (2013.01); *A61K 31/135* (2013.01); *A61K 31/185* (2013.01); *A61K 31/366* (2013.01); *A61K 31/40* (2013.01); *A61K 31/403* (2013.01); *A61K 31/4168* (2013.01); *A61K 31/437* (2013.01); *A61K 31/4425* (2013.01); *A61K 31/573* (2013.01); *A61K 31/65* (2013.01); *A61P 25/28* (2018.01)

(58) Field of Classification Search
CPC ...... A61K 31/423; A61K 31/433; A61P 25/28
See application file for complete search history.

(56) References Cited

U.S. PATENT DOCUMENTS

| 4,849,222 | A | | 7/1989 | Broaddus |
| 5,100,669 | A | | 3/1992 | Hyon |
| 5,814,344 | A | | 9/1998 | Tice |
| 2022/0016099 | A1 | * | 1/2022 | Shin ......................... A61P 3/10 |

FOREIGN PATENT DOCUMENTS

| KR | 10-2020-0069208 | A1 | | 6/2020 | |
| WO | 9307861 | A1 | | 4/1993 | |
| WO | 9511010 | A1 | | 4/1995 | |
| WO | 2008021210 | A2 | | 2/2008 | |
| WO | 2010021693 | A2 | | 2/2010 | |
| WO | WO-2010015037 | A1 | * | 2/2010 | ......... A61K 31/4741 |
| WO | 2013163455 | A2 | | 10/2013 | |

(Continued)

OTHER PUBLICATIONS

Sebastien Jacquemont et al.,Epigenetic Modification of the FMR1 Gene in Fragile X Syndrome is Associated with Differential Response to the mGluR5 Antagonist AFQ056, research article, 2011, 11 pages, Science Translational Medicine, New York, USA.

T.D. Aumann et al, SK channel function regulates the dopamine phenotype of neurons in the substantia nigra pars compacta, journal, Jan. 23, 2008, 12 pages, Experimental Neurology, Victoria, Australia.

Paul J. Benke et al, Biotin and Acetazolamide for Treatment of an Unusual Case of Autism with Lack of Nail and Hair Growth, Manuscript, Oct. 13, 2017, 10 pages, Pediatric Neurology, USA.

European Search Report dated Mar. 16, 2020 for Univ Bordeaux, Assetsup, and Centre Nat Rech Scient, European Patent Application No. EP19197502.8, filed Sep. 16, 2019.

(Continued)

*Primary Examiner* — James D. Anderson
(74) *Attorney, Agent, or Firm* — LAW OFFICES OF ALBERT WAI-KIT CHAN, PLLC

(57) ABSTRACT

The present invention relates to compounds and compositions for use in a method of treating and/or preventing neurological or non-neurological channelopathies, i.e., pathologies which are caused specifically by defects in some of the calcium-activated potassium channels. Specific neurological channelopathies and/or synaptopathies targeted by the present invention include specific neuropsychiatric pathologies, such as particularly Fragile X Syndrome (FXS), Angelman syndrome, Williams-Beuren syndrome, autism, Autism spectrum disorders (ASDs), hyperacusis, Smith-Magenis syndrome, Prader-Willi syndrome, 7q11.23 duplication syndrome, and cri-du-chat syndrome, as well as other neuropathic disorders such as trembling, epilepsy and neuropathic pains associated and neurodegenerative diseases such as Parkinson's and Alzheimer diseases. Compounds, compositions and methods of the present invention are also particularly useful and efficient in alleviating neurological symptoms common to these neuropsychiatric pathologies.

14 Claims, 15 Drawing Sheets

(56) References Cited

FOREIGN PATENT DOCUMENTS

| WO | 2016138138 | A1 | 9/2016 |
| WO | 2020116742 | A1 | 6/2020 |

OTHER PUBLICATIONS

International Preliminary Report on Patentability dated Mar. 15, 2022 for Universite De Bordeaux, International Application No. PCT/EP2020/075754, filed Sep. 15, 2020.
International Search Report dated Dec. 11, 2020 for Universite De Bordeaux, International Application No. PCT/EP2020/075754, filed Sep. 15, 2020.

* cited by examiner

A. *Macro-orchidism*

B. *Body Weight*

METHODS OF TREATMENT AND/OR PREVENTION OF DISORDERS AND SYMPTOMS RELATED TO BKCa AND/OR SK CHANNELOPHATHIES

FIELD OF THE INVENTION

The present invention relates to compounds and compositions for use in a method of treating and/or preventing neurological or non-neurological channelopathies, i.e., pathologies which are caused specifically by defects in some of the calcium-activated potassium channels. Specific neurological channelopathies and/or synaptopathies targeted by the present invention include specific neuropsychiatric pathologies, such as particularly Fragile X Syndrome (FXS), Angelman syndrome, Williams-Beuren syndrome, autism, Autism spectrum disorders (ASDs), hyperacusis, Smith-Magenis syndrome, Prader-Willi syndrome, 7q11.23 duplication syndrome, and cri-du-chat syndrome, as well as other associated neuropathic disorders such as trembling, epilepsy and neuropathic pains and neurodegenerative diseases such as Parkinson's and Alzheimer diseases. Compounds, compositions and methods of the present invention are also particularly useful and efficient in alleviating neurological symptoms common to these neurological pathologies.

BACKGROUND OF THE INVENTION

Neuropsychiatric pathologies are diseases of the central and peripheral nervous system: the brain, spine and cranial and peripheral nerves, neuromuscular junction and muscles. There are more than 600 diseases of the nervous system, with a complex etiology they are always difficult to classify. The specific causes of neurological problems may include genetic disorders, congenital abnormalities, infections, environmental health problems, brain injury, etc.

Specific neuropsychiatric pathologies including particularly Fragile X Syndrome (FXS), Angelman syndrome, Williams-Beuren syndrome, autism, Autism spectrum disorders (ASDs), hyperacusis, Smith-Magenis syndrome, Prader-Willi syndrome, 7q11.23 duplication syndrome, and cri-du-chat syndrome may be channelopathies, which are synaptopathies caused by deficiencies of specific calcium-activated potassium channels. Such channelopathies may indeed affect hyperpolarization and structure of neurons, particularly their dendrites, and glutamate release at the synapses, thereby causing altered synaptic function as primary neuropathology.

Despite the wide spectrum of experimental compounds tested in clinical trials, there is still no proven pharmacological treatment available for these neuropsychiatric pathologies, since many clinical trials with high expectations of success have failed to demonstrate significant improvements. While some of these trials showed some promising findings in smaller open-label trials, controlled trials only showed modest global benefits and almost none of these success stories were reproduced in the larger, placebo-controlled clinical trials that followed. Indeed, many trials were terminated because they did not meet their predesignated primary endpoints.

Many classes of psychiatric drugs are used in clinical practice to treat physical and behavioural symptoms in both patient populations. Most symptoms of these neurological and mental development disorders are managed using pharmacologic interventions, such as stimulants for attention deficits and hyperactivity, selective serotonin reuptake inhibitors (SSRIs) for anxiety, antipsychotic drugs for aggression and mood instability. For mental retardation in general, currently available treatment regimens include, for example, behavioural modifications and a range of medications including antidepressant and antipsychotic drugs. These pharmacologic treatments target only minor behavioural symptoms and not the core impairments or the underlying brain deficits.

Cognitive behavioural therapy has been used to improve language and socialization in some of these neurodevelopmental pathologies. Interventional services such as speech/language therapy, occupational therapy, physical therapy, special education services, and behaviour management are commonly used to address specific behavioural and neurodevelopmental issues.

In recent years, pharmacological treatment with the atypical antipsychotic risperidone has been commonly employed to augment non-pharmacological approaches in the treatment of individuals with autism. A randomized placebo-controlled trial of risperidone in autistic children demonstrated significant improvement on the irritability subscale of the Aberrant Behaviour Checklist and the Clinical Global Impressions-Improvement. However, adverse events included weight gain, increased appetite, fatigue, drowsiness, dizziness, and drooling. Social isolation and communication were not improved by administration of risperidone and adverse side effects such as extrapyramidal symptoms and dyskinesias have been associated with risperidone use in autistic children.

Even with substantial support and therapies, individuals affected by such neurological mental disorders continue to present significant impairments in their functioning throughout their life. In recent years, an effort to improve the quality of lives of the patients has driven increased research into the pathophysiologic causes and new therapeutic approaches to manage them. The results of these studies have provided some insight into the complexity of the relationship between genetic deficiency, downstream neurobiological abnormalities, and symptoms.

However, to this date, available treatment regimens for humans with these neuropsychiatric pathologies only assist in day-to-day functioning with a range of medications including anti-depressant and anti-psychotic drugs. However, such regimens frequently are not effective or may produce undesirable side-effects with long term use, particularly of anti-psychotic drugs. Thus, there is an urgent need to develop new and effective methods to treat these neurological pathologies.

SUMMARY OF THE INVENTION

The present invention relates to novel compositions for use in a method of treating and/or preventing Fragile X Syndrome (FXS), Angelman syndrome, Williams-Beuren syndrome, autism, Autism spectrum disorders (ASDs), hyperacusis, Smith-Magenis syndrome, Prader-Willi syndrome, 7q11.23 duplication syndrome, and cri-du-chat syndrome, comprising administering to a subject in need thereof a therapeutically effective amount of the said composition, wherein said composition comprises an agonist of the calcium-activated potassium channel (BKCa) and/or SK channel.

More specifically the agonist of the $Ca^{2+}$ activated $K^+$ channel is chosen among the compound having the following formula (I) or (II):

Formula (I)

wherein X represents a halogen selected among chloro, fluoro and bromo and wherein the radical R1 represents $NH_2$ or $=O$; and/or its pharmaceutically acceptable derivatives, tautomeric forms, isomers, polymorphs, prodrugs, metabolites, salts or solvates thereof.

Formula (II)

wherein the radical R2 is H or $NH_2$ and the radical R3 is H or $CH_3$, and/or its pharmaceutically acceptable derivatives, tautomeric forms, isomers, polymorphs, prodrugs, metabolites, salts or solvates thereof.

According to the present invention, preferred compounds of Formula (I) or (II) include chlorzoxazone or acetazolamide. Most preferred compound is compound of formula (I) and particularly chlorzoxazone.

An object of the present invention is to provide a composition for use in treating and/or preventing neuropsychiatric disorders, behavioural disorders and/or sensory hyperexcitability and more particularly such symptoms in neuropsychiatric pathologies such as in Fragile X Syndrome (FXS), Angelman syndrome, Williams-Beuren syndrome, autism, Autism spectrum disorders (ASDs), hyperacusis, Smith-Magenis syndrome, Prader-Willi syndrome, 7q11.23 duplication syndrome, and cri-du-chat syndrome, wherein the severity of one or more symptoms is alleviated or eliminated in said subject.

DETAILED DESCRIPTION OF THE INVENTION

Figure 1:
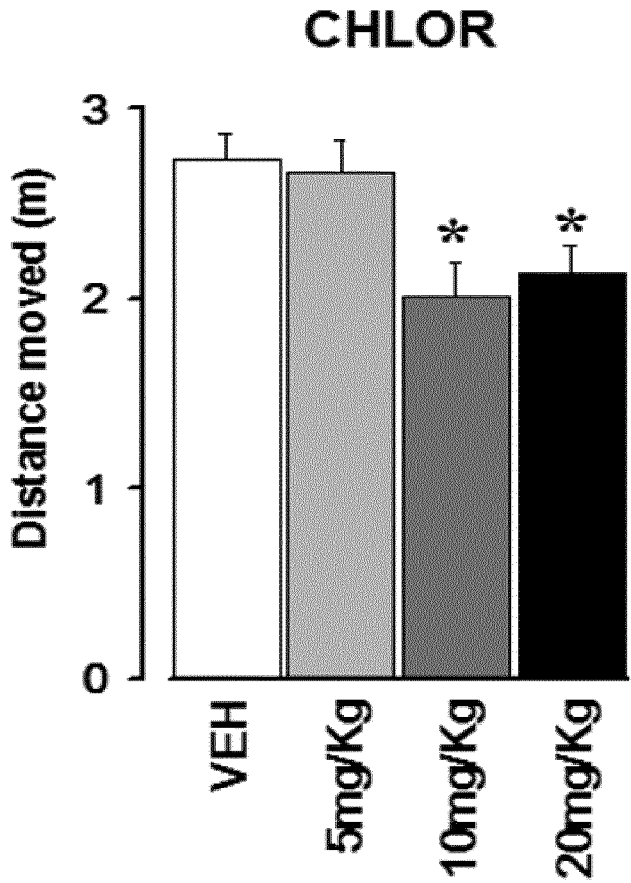
FIG. 1: is a graph showing the locomotor activity of WT mice in an open field test further acute administration of various doses of chlorzoxazone (CHLOR) (n=9-10; *=p<0.05, versus VEH and 5 mg/kg).

The present invention thus relates to a composition for use in a method of treating and/or preventing neuropsychiatric pathologies, and in particular channelopathies, comprising administering to a subject in need a therapeutically effective amount of a composition, wherein said composition comprises a compound which is an agonist or opener of the large-conductance calcium-activated potassium channel (BKCa channel) and/or of the small-conductance calcium-activated potassium channel (SK channel).

These specific neuropsychiatric pathologies can be synaptopathies which may be caused by BKCa and/or SK deficiencies. More precisely, these neuropsychiatric pathologies are selected among Fragile X Syndrome (FXS), Angelman syndrome, Williams-Beuren syndrome, autism, Autism spectrum disorders (ASDs), hyperacusis, Smith-Magenis syndrome, Prader-Willi syndrome, 7q11.23 duplication syndrome, and cri-du-chat syndrome which all present deficiencies at least of the BKCa channel and/or SK channel. These neuropsychiatric pathologies also present two common neurological symptoms: cognitive disorder and behavioural disorders. Most of the time, i.e. with a probability ranging from 60 to 100%, sensory hyperexcitability, such as increased sensitivity to ranges of sound intensity levels and/or ranges of frequencies that occurs for example in hyperacusis, is a third symptom.

Calcium-activated potassium channels correspond to a family of channels which are all activated by an increase of intracellular calcium ions. Based on their single channel conductance in symmetrical $K^+$ solutions, channels are divided into three subclasses: large conductance (BK)>150 pS; intermediate conductance (IK) 50-150 pS; and (SK) small conductance <50 pS. ("pS" stands for picosiemens, a unit of electrical conductance). These channels are found in the majority of the nerve cells, where they modulate action potential and neuronal excitability and plasticity. Two forms of synaptic plasticity, e.g., long-term potentiation (LTP) and long-term depression (LTD), have been characterized at several synapses in the mammalian brain and may represent physiological correlates of learning and memory. Many neurological diseases, including developmental disorders of cognition, are characterized by defects in synaptic plasticity.

BKCa or BK channels (e.g., large-conductance calcium-activated potassium channels or large conductance $Ca^{2+}$ activated $K^+$ channels) are activated in response to membrane depolarization and binding of intracellular $Ca^{2+}$ and $Mg^{2+}$ and are involved in the regulation of neurotransmitter release and neuronal excitability. These channels present three main structural domains: a voltage sensing domain which senses the membrane potential, the cytosolic domain which senses calcium ions and the pore-gate domain which is a membrane-spanning domain formed by four pore-forming beta subunits that are encoded by a single Slo1 gene. BK channels are widely distributed throughout the nervous system, where they play an important role in regulating neuronal action potential duration and pre-synaptic neurotransmitter release at the synapses.

SK channels (e.g., small-conductance calcium-activated potassium channels or small conductance $Ca^{2+}$ activated $K^+$ channels) are activated by an increase in the concentration of intracellular calcium, and they are characterized by their small unitary conductance and sensitivity to submicromolar $Ca^{2+}$. They are encoded by at least three genes SK1, SK2 and SK3 (or KCNN1, KCNN2, and KCNN3) and present four subunits which associate into homo- or heterotetramers and each of the subunits has six transmembrane hydrophobic alpha helical domains (S1 to S6) with a loop between S5 and S6 forms the potassium ion selectivity filter and calmodulin binding domain in a cytoplasmic C-terminus region. SK channels are expressed widely in different tissues, including nervous system, vascular endothelium, skeletal muscle, smooth muscle and cardiac myocytes. They are involved inter alia in regulating the post-hyperpolarization in the neurons of the CNS, and thus affecting excitability of neurons and synaptic transmission. They have been showed to be also involved in the atrial repolarization.

An "agonist," as used herein, is a compound that activates cell signaling. For example, a calcium-activated potassium channel receptor agonist activates cell signaling mediated through BKCa channel and SK channel.

Mental, behavioural and cognitive disorders are syndromes characterized by clinically significant disturbances in an individual's cognition, emotional regulation, or behaviour that reflects a dysfunction in the psychological, biological, or developmental processes that underlie mental and behavioural functioning. These disturbances are usually associated with distress or impairment in personal, family, social, educational, occupational, or other important areas of functioning.

Intellectual disability (ID) is a neurodevelopmental disorder characterized by deficits in cognition, deficits in adaptive function with a low IQ, and/or significant limitations both in intellectual functioning (reasoning, learning, problem solving) and/or in adaptive behaviour, which covers a range of everyday social and practical skills. It is also called mental retardation. Diseases associated with ID are often difficult to detect and diagnose thereby delaying appropriate treatment for ID and the underlying diseases that are responsible for ID. The term "Mental retardation" means that a subject has lower than average intelligence. Intelligence describes a subject's ability to think, learn and solve problems. A subject with mental retardation may have difficulty in learning, may take longer to learn social skills, such as how to communicate, and may be less able to care for himself or herself and to live on his or her own as an adult.

Fragile X Syndrome (FXS) is one of the most common causes of inherited intellectual disabilities and one of the most studied synaptopathies. It has now been established that fragile X mental retardation protein (FMRP), the protein that lacks in FXS, plays a key role in regulating synaptic connectivity and function. Alteration of LTD is a prominent feature of fragile X syndrome. It is characterized by a constriction near the end of the long arm of the X chromosome that gave it a "fragile" appearance. This constriction arises from the expansion of the trinucleotide repeat sequence (CGG) in the 50 untranslated region (UTR) of the fragile X mental retardation gene (FMR1) that results in its silencing and the near complete loss of FMRP. Subjects with FXS may develop fragile X-associated tremor/ataxia syndrome (FXTAS), which is characterized by progressive cerebellar ataxia, Parkinsonism, dementia and autonomic dysfunction. A definitive diagnosis of FXS is made through genetic testing to determine the number of CGG repeats.

Angelman syndrome (AS) is a complex genetic disorder that primarily affects the nervous system. Children with Angelman syndrome present delayed development, intellectual disability, severe speech impairment, ataxia, and most of them also have epilepsy events. This syndrome results from the loss of the gene UBE3A within chromosome 15, which should be fully active in the brain.

Autism spectrum disorder (ASD) is a range of neurological and mental development disorders that affect communication and behaviour, which includes autism and Asperger syndrome. It is known as a spectrum disorder because there is a wide variation in the type and severity of symptoms. In other words, ASDs affect each person in different ways and can range from very mild to severe. ASDs include Autistic Disorder (also called "classic" autism), Asperger Syndrome and Pervasive Developmental Disorder. People with ASDs share some similar symptoms, such as problems with social interaction and communication. But there are differences in when the symptoms start, how severe they are, and their exact nature. These symptoms are characterized by variable expression of traits that belong to the "autistic triad": impaired social skills, poor reciprocal communication and poor cognitive flexibility with limited interests and repetitive behaviours including stereotypies.

Williams-Beuren syndrome (WBS) is a developmental disorder characterized by mild to moderate intellectual disability or learning problems, unique personality characteristics, distinctive facial features, and heart and blood vessel (cardiovascular) problems. It is caused by the deletion of 26 to 28 genes within the long arm of one of the two chromosomes 7. Children with WBS present developmental delays which include delay of language abilities and delayed motor skill development. They also have higher anxiety levels as well as phobia development, which may be associated with hyperacusis.

Smith-Magenis syndrome (SMS) is a developmental disorder caused by a deletion of a small piece of chromosome 17 and particularly of the gene RAI1 (Retinoic acid induced 1 gene) which appears to play an important role in the development of the brain. The major features of this condition include mild to moderate intellectual disability, delayed speech and language skills, distinctive facial features, sleep disturbances, and behavioural problems.

Prader-Willi syndrome is a complex genetic disorder that affects many parts of the body including the nervous system characterized by delayed development, mild to moderate intellectual impairment and learning disabilities. Other symptoms include muscular hypotonia and hyperphagia. This syndrome is caused by loss of function of several genes on chromosome 15, possibly of the genes of the SNORD116 cluster.

7q11.23 duplication syndrome is a condition that can cause a variety of neurological and behavioural abnormalities. People with 7q11.23 duplication syndrome typically have delayed development of speech and motor skills. Intellectual development varies widely in 7q11.23 duplication syndrome. Behavioural problems associated with this condition include anxiety disorders, attention deficit hyperactivity disorder (ADHD), and autistic behaviour. This syndrome results from an extra copy of a region of the long arm of chromosome 7 and particularly of the ELN and GTF21 genes. Of note this is the same region which causes WBS when deleted.

Cri-du-chat (cat's cry) syndrome is a genetic neuropsychiatric pathology often characterized by children having a high-pitched cry that sounds like that of a cat. The disorder is characterized by intellectual disability and delayed development, microcephaly, and hypotonia. It is also known as 5p– (5p minus) syndrome as it is caused by a deletion of the end of the short (p) arm of chromosome 5. Loss of the gene CTNND2 is associated in particular with severe intellectual disability in some people with this condition. The size of the deletion varies among affected individuals with larger deletions resulting in more severe intellectual disability and developmental delay than smaller deletions.

Hyperacusis is characterized by a high sensitivity to certain frequencies and volume ranges of sound. Hyperacusis can result in anxiety, stress and even panic attacks.

Most interestingly, these aforementioned neurodevelopmental pathologies have been found to present two specific common neurological symptoms: cognitive disorder and behavioural disorder. Most of the time, i.e. with a probability ranging from 60 to 100%, sensory hyperexcitability, they present a third specific symptom: sensory hyperexcitability, such as increased sensitivity to ranges of sound intensity levels and/or ranges of frequencies.

Applicants found that compounds and compositions according to the present invention are capable of efficiently activating BKCa and/or SK channels and thus are useful in treating and/or preventing selected neuropsychiatric pathologies among Fragile X Syndrome (FXS), Angelman syndrome, Williams-Beuren syndrome, autism, Autism spectrum disorders (ASDs), hyperacusis, Smith-Magenis syndrome, Prader-Willi syndrome, 7q11.23 duplication syndrome, and cri-du-chat syndrome.

Most importantly, compounds and compositions according to the present invention are also useful in substantially alleviating at least one of the three common identified symptoms either cognitive disorder, behavioural disorder, and/or sensory hyperexcitability such as increased sensitivity to certain frequencies and volume ranges of sound.

The present invention thus relates to compounds and compositions for use in a method of treating and/or preventing neuropsychiatric pathologies selected among Fragile X Syndrome (FXS), Angelman syndrome, Williams-Beuren syndrome, autism, Autism spectrum disorders (ASDs), hyperacusis, Smith-Magenis syndrome, Prader-Willi syndrome, 7q11.23 duplication syndrome, and cri-du-chat syndrome, comprising administering to a subject in need a therapeutically effective amount of the composition, or for alleviating at least one symptom thereof selected among cognitive disorder, behavioural disorder, and/or sensory hyperexcitability, such as increased sensitivity to certain frequencies and volume ranges of sound, wherein said composition comprises a compound which is an agonist or opener of the large-conductance calcium-activated potassium channel (BKCa channel) and/or of the small-conductance calcium-activated potassium channel (SK channel).

Other neurological channelopathies which may be treated and/or prevented according to the present invention include trembling, epilepsy and neuropathic pains associated with CNS lesions or dysfunctions. Other neurological degenerative pathologies such as Parkinson's and Alzheimer's diseases are also concerned, since subgroups of patients presented anomalies or dysfunctions of the BKCa and/or SK channels. In particular, these channels are thought to be involved in the neuroinflammatory mechanisms of Parkinson's and Alzheimer's diseases. Indeed, the inflammation-mediated degeneration has been clearly identified for both diseases: in Parkinson's disease (PD) it generally occurs together with the loss of dopaminergic receptors, while chronic neuroinflammation causes synaptic dysfunction and neuronal cell death in Alzheimer's disease (AD).

Therefore, the present invention also relates to a composition for use in a method of treating and/or preventing trembling, epilepsy and neuropathic pains associated with CNS lesions or dysfunctions, Parkinson's and Alzheimer's diseases, comprising administering to a subject in need a therapeutically effective amount of the composition, wherein said composition comprises a compound which is an agonist or opener of the large-conductance calcium-activated potassium channel (BKCa channel) and/or of the small-conductance calcium-activated potassium channel (SK channel).

The present invention further relates to a composition for use in a method of treating and/or preventing non-neurological pathologies which are caused by de novo mutations of the BKCa or SK channels wherein said composition comprises a compound which is an agonist or opener of the large-conductance calcium-activated potassium channel (BKCa channel) and/or of the small-conductance calcium-activated potassium channel (SK channel). Such pathologies include specifically primary or essential hypertension, diastolic hypertension, cardiomyopathy, renal damage, electrolyte imbalance, and asthma.

Said compositions for use in a method according to the present invention may comprise a compound having the following formula (I) or (II):

formula (I)

wherein X represents a halogen, wherein the radical R1 represents NH$_2$ or =O;

formula (II)

wherein the radical R2 is H or NH$_2$ and the radical R3 is H or CH$_3$.

Compounds of formula (I) according to the present invention may comprise a halogen atom chosen among chloro, fluoro, or bromo. Alternatively, the radical X may be any functional equivalents which can prevent hydroxylation of the molecule by a cytochrome, thereby decreasing the hepatic metabolism with a resulting increase in the active fraction of the molecule.

Preferred compound of formula (I) is the chlorzoxazone or 5-chloro-3H-1,3-benzoxazol-2-one, wherein the radical X is a chloro and R1 is a carbonyl.

Preferred compound of formula (II) is the acetazolamide, or N-(5-sulfamoyl-1,3,4-thiadiazol-2-yl) acetamide, wherein R2 is NH$_2$ and R3 is CH$_3$.

Preferred compositions for use in a method of treating and/or preventing Fragile X Syndrome (FXS), Angelman syndrome, Williams-Beuren syndrome, autism, Autism spectrum disorders (ASDs), hyperacusis, Smith-Magenis syndrome, Prader-Willi syndrome, 7q11.23 duplication syndrome, and cri-du-chat syndrome comprise administering to a subject in need a therapeutically effective amount of the chlorzoxazone or the acetazolamide, or a pharmaceutically acceptable derivative, tautomeric form, isomer, polymorph, prodrug, metabolite, salt or solvate thereof.

Most preferred compositions for use in a method according to the present invention comprise an effective amount of chlorzoxazone.

According to the present invention, specific agonists of the BKCa channel and/or SK channel are selected among compounds of formula (I) and (II) were particularly effective for treating and/or preventing Fragile X Syndrome (FXS), Angelman syndrome, Williams-Beuren syndrome, autism, Autism spectrum disorders (ASDs), hyperacusis, Smith-Magenis syndrome, Prader-Willi syndrome, 7q11.23 duplication syndrome, and cri-du-chat syndrome, and significantly improved at least one of the common symptoms including cognitive disorder, behavioural disorder, and/or sensory hyperexcitability, such as increased sensitivity to certain frequencies and ranges of sound intensity levels.

Importantly, compounds of formula (I) and (II) are agonists of BKCa channel and agonists of SK channel as well and thus can advantageously activate two of the channels involved in said neuropsychiatric pathologies, thereby resulting in a synergistic therapeutic activity and in superior effects for alleviating common symptoms of these disorders.

Chlorzoxazone and acetazolamide are two compounds selected from the numerous lists and very diverse classes of compounds acting as agonists/openers of Ca2+ activated K+ channels and SK channels. They have been selected for use in the method of the present invention since, as indicated above, Applicant was able to show superior results and efficacy of these compounds for treating and/or preventing Fragile X Syndrome (FXS), Angelman syndrome, Williams-Beuren syndrome, autism, Autism spectrum disorders (ASDs), hyperacusis, Smith-Magenis syndrome, Prader-Willi syndrome, 7q11.23 duplication syndrome, and cri-du-chat syndrome as well as further synaptopathies or channelopathies cited above.

By way of examples of the numerous lists and diverse classes of agonists of the BKCa, we can cite nicorandil, diazoxide, minoxidil, pinacidil, aprikalim, cromokulim and derivative U-89232, P-1075 (a selective plasma membrane KATP channel opener), emakalim, YM-934, (+)-7,8-dihydro-6,6-dimethyl-7-hydroxy-8-(2-oxo-1-piperidinyl)-6H-pyrano[2,3-f]benz-2,1,3-oxadiazole (NIP-121), R0316930, RWJ29009, SDZPCO400, rimakalim, symakalim, YM099, 2-(7,8-dihydro-6,6-dimethyl-6H-[1,4]oxazino[2,3 -f][2,1,3] benzoxadiazol-8-yl) pyridine N-oxide, 9-(3-cyanophenyl)-3,4,6,7,9,10-hexahydro-1,8-(2H,5H)-acridinedione (ZM244085), [(9R)-9-(4-fluoro-3-125iodophenyl)-2,3,5,9-tetrahydro-4H-pyrano[3,4-β]thieno[2,3-e]pyridin-8(7H)-one-1,1-dioxide]([125I]A-312110), (−)N-(2-ethoxy phenyl)-N'-(1,2,3-trimethylpropyl)-2-nitroethene-1,1-diamine (BayX 9228), N-(4-benzoyl phenyl)-3,3,3-trifluoro-2-hydroxy-2-methylpropionamine (ZD6169), ZD6169 (KATP opener) and ZD0947 (KATP opener), WAY-133537 and a novel dihydropyridine potassium channel opener, A-278637, benzimidazolone derivatives NS004 (5-trifluoromethyl-1-(5-chloro-2-hydroxyphenyl)-1,3-dihydro-2H-benzimidazole-2-one), NS 1619 (1,3-dihydro-1-[2-hydroxy-5-(trifluoromethyl)phenyl]-5-(trifluoromethyl)-2H-benzimidazol-2-one), NS1608 (N-(3-(trifluoromethyl) phenyl)-N'-(2-hydroxy-5-chlorophenyl)urea), BMS-204352, retigabine (also GABA agonist), intermediates such as benzoxazoles and zoxazolamine, etc.

One of the selected compounds for use in the method according to the present invention, chlorzoxazone belongs to the oxazolidinone family of drugs and has been registered and administered for its muscle relaxant properties, analgesic properties or tranquilizer properties. Other drugs of the same family include the metaxalone—the most commonly used—as well as the 6-benzoylbenzoxazolone, and the mephenoxalone. Chlorzoxazone is currently marketed under the trade names LORZONE®, PARAFLEX® and MUS-COL® and in combination form as PARAFON FORTE®, a combination of chlorzoxazone and acetominophen (paracetamol).

Acetazolamide is thus the second compound selected for use in a method according to the present invention and it is currently registered and marketed under the tradenames DIAMOX® or SEQUELS® sustained release capsules for the control of fluid secretion (e.g., some types of glaucoma), the treatment of certain convulsive disorders (e.g. epilepsy) and the promotion of diuresis in instances of abnormal fluid retention (e.g., cardiac oedema). Indications and usage of acetazolamide thus include adjunctive treatment of oedema due to congestive heart failure, drug-induced oedema; centrencephalic epilepsies, chronic simple glaucoma, secondary glaucoma and preoperatively in acute angle-closure glaucoma where delay of surgery is desired in order to lower intraocular pressure and for the treatment of acute altitude sickness.

However, it was never shown or suggested that these specific two agonists would have such superior activity for treating and/or preventing Fragile X Syndrome (FXS), Angelman syndrome, Williams-Beuren syndrome, autism, Autism spectrum disorders (ASDs), hyperacusis, Smith-Magenis syndrome, Prader-Willi syndrome, 7q11.23 duplication syndrome, and cri-du-chat syndrome as well as further synaptopathies or channelopathies cited above.

Preferably, the present invention relates to compositions for use in a method of treating and/or preventing Fragile X Syndrome (FXS), Williams-Beuren syndrome , and hyperacusis comprising administering to a subject in need a therapeutically effective amount of the chlorzoxazone or the acetazolamide, or a pharmaceutically acceptable derivative, tautomeric form, isomer, polymorph, prodrug, metabolite, salt or solvate thereof. Most preferably, the present invention relates to compositions for use in a method of treating and/or preventing FXS or defects associated with FMR1 gene comprise administering to a subject in need a therapeutically effective amount of the chlorzoxazone or the acetazolamide, or a pharmaceutically acceptable derivative, tautomeric form, isomer, polymorph, prodrug, metabolite, salt or solvate thereof.

Fragile X syndrome is the most widespread single-gene cause of autism and inherited cause of mental retardation among children. Anyone with the FMR1 gene mutation can pass it to their children. Approximately 1 in 4,000 males and 1 in 8,000 females have Fragile X syndrome, according to Centers for Disease Control and Prevention (CDC). Not everyone with the mutation will show signs or symptoms of Fragile X, and disabilities will range from mild to severe as well as physical characteristics such as an elongated face, large or protruding ears, large testes (macroorchidism), and behavioural characteristics such as stereotypic movements (e.g., hand-flapping), and social anxiety.

Fragile X results from a change or mutation in the Fragile X Mental Retardation 1 (FMR1) gene, which is found on the X chromosome. The gene normally codes for a protein called Fragile X Mental Retardation Protein, or FMRP. This protein is important for creating and maintaining connections between cells in the brain and nervous system. The mutation causes the body to make only a little bit or none of the protein, which often causes the symptoms of Fragile X. Studies have shown a relationship between intelligence quotient (IQ) and the level of FMRP, with higher levels of FMRP being associated with less cognitive impairment. In general, the signs and symptoms of Fragile X fall into five categories: deficits in (1) intelligence and learning, (2) speech and language, (3) physical alterations, (4) social, emotional and (5) sensory abnormalities. Individuals with Fragile X have impaired intellectual functioning, social anxiety, language difficulties and abnormal sensitivity to certain stimuli.

As used herein, the term "defects associated with FMR1 gene" refers to a disease or disorder that results from transcriptional inactivation of the FMR1 gene. Generally, inactivation of the FMR1 gene results in the loss of production of fragile X mental retardation protein (FMRP) and causes a range of developmental problems including learning disabilities and cognitive impairment, moderate to severe mental retardation, ataxia (e.g., loss of coordination), tremor, memory loss, loss of sensation in the lower extremities (e.g., peripheral neuropathy), mental and behavioural changes, and polycystic ovarian syndrome. Generally, severity of "defects associated with FMR1 gene" can be classified by the number of polymorphic CGG repeats present in the 5'UTR of a subject's FMR1 gene. The number of repeats in the expansion can vary. In some embodiments, the number of CGG repeats in the expansion ranges from about 55 to about 500 repeats. In some embodiments, a subject is referred to as "premutation" if the number of CGG repeats ranges from about 55 repeats to about 200 repeats. Premutation subjects are susceptible to conversion to full mutation status and are thus at increased risk of developing FXS compared to subjects having normal alleles (e.g. having between 6 and 54 CGG repeats). In some embodiments, the number of CGG repeats is greater than 200 repeats, and the subject is referred to as having a "full mutation". Full mutation subjects have FXS. In some embodiments, the number of CGG repeats in a subject having FXS ranges from about 201 to about 500 repeats. In some embodiments, the number of CGG repeats is greater than 500 repeats.

FXS also often occurs with other pathological conditions. These may include anxiety, attention-deficit/hyperactivity disorder (ADHD), depression, cerebral palsy, difficult peer relationships, intellectual and learning disabilities. Furthermore, some syndromes are associated with mental disability or retardation, which may or may not be co-existing with FXS, but nevertheless may be treatable according to the present invention. These syndromes include Alstrom syndrome, Bannayan-Riley-Ruvalcaba syndrome, Bardet-Biedel syndrome, Rett syndrome, Beckwith-Wiedemann syndrome, Cerebral Palsy, Cohen syndrome, Cerebral dysgenesis, Childhood Disintegrative Disorder, Coffin-Lowry syndrome, Down syndrome, Duchenne/Becker muscular dystrophies, Joubert syndrome, Lujan-Fryns syndrome, Lesch-Nyhan syndrome, Meningomyelocele, Neurofibromatosis, Noonan syndrome, Nance-Horan syndrome, Orstavik syndrome, PTEN mutations, Rubinstein-Taybi syndrome, Smith-Lemli-Opitz syndrome, Sotos syndrome, Velocardiofacial syndrome, Shprintzen syndrome, 22q deletion syndrome, DiGeorge syndrome, X-linked adenoleukodystrophy, Zellweger syndrome.

The present invention also provides compounds and compositions for use in a method of alleviating at least one of the FXS symptoms chosen among cognitive disorder, behavioural disorder, and/or sensory hyperexcitability, such as increased sensitivity to certain frequencies and/or ranges of sound intensity levels.

Individuals with FXS generally also exhibit several other symptoms, including (i) mental retardation with learning difficulties and reading delays, (ii) behavioural disorders including irritability, anxiety, attention deficit, hyperactive behaviours, and autism spectrum disorders (ASDs), (iii) heightened sensitivity to sensory stimuli, such as tactile irritation, hyperacusis, audiogenic seizures, tinnitus, and nystagmus, (iv) dyskinesia, tremor activity. Non-neurological symptoms include a long face, large ears, hyperextensible joints, and enlarged testes in post-pubescent males. In addition, brain autopsies show that dendritic spines are longer and immature in appearance.

Other symptoms of FXS may further include obsessive-compulsive disorder, a sensory hyperarousal disorder, an anxiety disorder, seizure disorder, irritability, aggression, startle tremor, repetitive/self-stimulatory behaviour, eye diversion, hand biting, hitting of the head and hitting others, tremors, rigidity, ataxia, bradykinesia, gait, speech impairment, vocalization difficulties, cognition impairment, impaired motor activity, clinical seizure, hypotonia, hypertonia, feeding difficulty, drooling, hand flapping, easily provoked laughter, short attention span, reduced sensation, numbness or tingling, pain, muscle weakness in the lower limbs, inability to control the bladder or bowel, chronic pain syndromes, fibromyalgia, migraine, hypothyroidism, hypertension, vertigo, olfactory dysfunction, hearing loss, short-term memory loss, loss of executive function, impulse control difficulties, self-monitoring difficulties, attention focusing difficulties, cognitive inflexibility, anxiety, depression, moodiness, irritability.

More particularly, compositions and methods according to the present invention are useful in alleviating one or more behavioural symptoms of Fragile X Syndrome which can include an improvement in a total score of an Anxiety, Depression and Mood Scale (ADAMS). In some embodiments, alleviating one or more behavioural symptoms of FXS can include improvement in one or more subscales of ADAMS. Alleviating one or more behavioural symptoms of Fragile X Syndrome can include improvement in one or more measures of an Aberrant Behaviour Checklist for Fragile X (ABC-FXS).

The Anxiety, Depression, and Mood Scale (ADAMS) is an instrument that is used by clinicians, doctors, and researchers to assess the level of anxiety, depression, and mood in patients with intellectual disabilities, including FXS. ADAMS consists of questions grouped into five subscales, including (i) general anxiety, (ii) social avoidance, (iii) compulsive behaviour, (iv) manic/hyperactive behaviour, and (v) depressed mood. Each question is answered by a clinician/doctor on a four-point scale ranging from 0 ("not a problem") to 3 ("severe problem"). In addition to subscale scores, the ADAMS yields a total score.

Furthermore, the compounds and compositions according to the present invention may be used in a method of improving one or more behavioural traits which are assessed by one or more of: CARS behaviour T-Score; ADI-R Reciprocal Social Interaction and/or Total score; SCQ Communication Score; VABS II Adaptive Behaviour Composite, Communication Domain, Expressive Communication Subdomain, Personal Daily Living Skills Subdomain, Socialization Domain, Coping Skills Subdomain, and/or Fine Motor Skills Subdomain score(s); and/or CBCL Emotionally Reactive T-Score, in a subject in need thereof having intellectual disability including FXS and related disorders.

Intelligence Quotient (IQ) is a measure of the progress an individual had made in mental or cognitive development compared to same aged peers, and is used to make important decisions in clinical, psychoeducational, and research arenas. This score has an impact on the allocation of educational and clinical services, monitoring developmental progress or decline, and can significantly affect the results and interpretation of research. There is a decline in IQ score with increasing age in the FXS population. Mental retardation, defined as a failure to develop a sufficient cognitive and adaptive level, is one of the most common human lifelong disorders. According to estimates, 1-3% of the human population has an IQ below 70. Among people affected with FXS, intelligence quotient (IQ) scores decline noticeably with age: adolescents and adults consistently score lower on IQ tests than young children. While the average IQ score of the general population is 100, boys with FXS have an average IQ score under 55.

The Aberrant Behaviour Checklist (ABC) was "designed to assess behavioural concerns of adults within institutional settings." (Wheeler at page 142.) Since then, the original ABC has been adapted to address patients who are not institutionalized and specifically to address FXS. The Aberrant Behaviour Checklist-FXS Specific (ABC-FXS) scale is used by clinicians, doctors, and researchers to access certain behaviours in patients with FXS. The ABC-FXS scale has six subscales including (i) irritability, (ii) hyperactivity, (iii) socially unresponsive/lethargic, (iv) social avoidance, (v) stereotypy, and (vi) inappropriate speech. Like ADAMS, the ABC-FXS scale is a four-point Likert-type scale ranging from 0 (not a problem) to 3 (problem is severe). Other well-known scoring systems for measuring behavioural improvement can include at least one of Vineland, CARS, SCQ, CBCL, or ADI-R scores in the subject. More specifically measuring one or more of: CARS behaviour T-Score; ADI-R Reciprocal Social Interaction and/or Total score; SCQ Communication Score; VABS II Adaptive Behaviour Composite, Communication Domain, Expressive Communication Subdomain, Personal Daily Living Skills Subdomain, Socialization Domain, Coping Skills Subdomain, and/or Fine Motor Skills Subdomain score(s); and/or CBCL Emotionally Reactive T-Score.

Compositions according to the present invention may also comprise a carrier or excipient, preferably a pharmaceutically acceptable carrier or excipient. Pharmaceutical compositions of the present invention are thus particularly suitable for a subject which is a human or non-human animal subject.

Both compounds chlorzoxazone and acetazolamide are available for oral administration, such as tablets, sustained release capsules etc. . . and thus are preferably administered via oral routes to patients according to the present invention.

Possible alternative routes of administration of the compositions are also envisaged and would include oral, topical, parenteral or mucosally (e.g., buccally, by inhalation, or rectally) administrations in dosage unit formulations containing conventional non-toxic pharmaceutically acceptable carriers.

As indicated above, in case of oral administrations, the compounds may be present for example in the form of a capsule, a tablet, or the like, or as a semi-solid or liquid formulation (see Remington's Pharmaceutical Sciences, Mack 5 Publishing Co., Easton, Pa.). Alternatively, they may be administered in the form of a time-controlled release tablet, including but not limited to diffusion-controlled systems, osmotic devices, dissolution-controlled matrices, and erodible/degradable matrices.

For oral administration either in the form of a tablet or capsule, the compositions may comprise non-toxic, pharmaceutically acceptable excipients such as binding agents (e.g., pregelatinized maize starch, polyvinylpyrrolidone or hydroxypropyl methylcellulose); fillers (e.g., lactose, sucrose, glucose, mannitol, sorbitol and other reducing and non-reducing sugars, microcrystalline cellulose, calcium sulfate, or calcium hydrogen phosphate); lubricants (e.g., magnesium stearate, talc, or silica, steric acid, sodium stearyl fumarate, glyceryl behenate, calcium stearate, and the like); disintegrants (e.g., potato starch or sodium starch glycolate); or wetting agents (e.g., sodium lauryl sulphate), colouring and flavouring agents, gelatine, sweeteners, natural and synthetic gums (such as acacia, tragacanth or alginates), buffer salts, carboxymethylcellulose, polyethylene glycol, waxes, and the like.

The tablets can be coated by methods well known in the art. The cores are generally coated with a concentrated sugar solution which may contain e.g., gum arabic, gelatine, talcum, titanium dioxide, and the like. Alternatively, the tablets can be coated with a polymer known to a person skilled in the art, wherein the polymer is dissolved in a readily volatile organic solvent or mixture of organic solvents. In preferred embodiments, the chlorzoxazone or acetazolamide is formulated in to immediate-release (IR) or modified-release (MR) tablets. Immediate release solid dosage forms permit the release of most or all active ingredient over a short period of time, such as 60 minutes or less, and make rapid absorption of the drug possible. Modified release solid oral dosage forms permit the sustained release of the active ingredient over an extended period of time in an effort to maintain therapeutically effective plasma levels over similarly extended time intervals and/or to modify other pharmacokinetic properties thereof.

For the formulation of soft gelatin capsules, the chlorzoxazone or acetazolamide may be admixed with a vegetable oil or poly-ethylene glycol. Hard gelatin capsules may contain granules of the chlorzoxazone or acetazolamide using either the above-mentioned excipients for tablets e.g., lactose, saccharose, sorbitol, mannitol, starches (e.g., potato starch, corn starch or amylopectin), cellulose derivatives or gelatin. Also, liquids or semisolids of the drug can be filled into hard gelatin capsules.

The pharmaceutical compositions of the present invention may also be introduced in microspheres or microcapsules, e.g., fabricated from polyglycolic acid/lactic acid (PGLA) (U.S. Pat. Nos. 5,814,344; 5,100,669 and 4,849,222; international publications WO95/11010 and WO93/07861). Biocompatible polymers useful in achieving controlled release of a drug, include for example, polylactic acid, polyglycolic acid, copolymers of polylactic and polyglycolic acid, poly-epsilon caprolactone, polyhydroxybutyric acid, polyorthoesters, polyacetals, polyhydropyrans, polycyanoacrylates, and cross-linked or amphipathic block copolymers of hydrogels.

Liquid pharmaceutical compositions for oral administration can take the form of, for example, solutions, syrups, emulsions or suspensions, or they can be presented as a dry product for reconstitution with water or other suitable vehicle before use. Preparations for oral administration can be suitably formulated to give controlled or postponed release of the active compound. For oral administration in liquid form, the active ingredient can be combined with non-toxic, pharmaceutically acceptable inert carriers (e.g., ethanol, glycerol, water), suspending agents (e.g., sorbitol syrup, cellulose derivatives or hydrogenated edible fats), emulsifying agents (e.g., lecithin or acacia), non-aqueous vehicles (e.g., almond oil, oily esters, ethyl alcohol or fractionated vegetable oils), preservatives (e.g., methyl or propyl-p-hydroxybenzoates or sorbic acid), and the like. Stabilizing agents such as antioxidants (BHA, BHT, propyl gallate, sodium ascorbate, citric acid) can also be added to stabilize the dosage forms. For example, solutions may contain from about 0.1% to about 90% by weight of active ingredient, with the balance being sugar and mixture of ethanol, water, glycerol and propylene glycol. Optionally such liquid pharmaceutical compositions may contain colouring agents, flavouring agents, saccharine and carboxymethyl-cellulose as a thickening agent or other excipients known to a person skilled in the art.

For administration by inhalation, active ingredient can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, e.g., gelatine for use in an inhaler or insufflator can be formulated containing a powder mix of the compound and a suitable powder base such as lactose or starch.

Solutions for parenteral applications by injection can be prepared in an aqueous solution of active substances, preferably in a concentration of from about 0.5% to about 10% by weight. These solutions may also contain stabilizing agents and/or buffering agents and may conveniently be provided in various dosage unit ampoules.

The compositions of the present invention can be delivered parenterally, i.e., by intravenous (i.v.), intracerebroventricular (i.c.v.), subcutaneous (s.c.), intraperitoneal (i.p.), intramuscular (i.m.), subdermal (s.d.), or intradermal (i.d.) administration, by direct injection, via, for example, bolus injection or continuous infusion. Formulations for injection can be presented in unit dosage form, e.g., in ampoules or in multi-dose containers, with an added preservative.

Other preferred compositions are formulated for administration via intranasal, intratracheal, mucosal, transmucosal, buccal, sublingual, pulmonary, intrabronchial, intrapulmonary routes. Particularly preferred are compositions wherein said composition is liquid or aerosol and is formulated in a spray, droplet, colloidal, mist, nebulae, in atomized vapor, etc.

Optimal therapeutically effective amount should be determined experimentally, taking into consideration the exact mode of administration, from in which the drug is administered, the indication toward which the administration is directed, the subject involved (e.g., body weight, health, age, sex, etc.), and the preference and experience of the physician or veterinarian in charge. Toxicity and therapeutic efficacy of the compositions of the invention can be determined by standard pharmaceutical procedures in experimental animals, e.g., by determining the $LD_{50}$ (the dose lethal to 50% of the population and the $ED_{50}$ (the dose therapeutically effective in 50% of the population). The dose ratio between therapeutic and toxic effects is the therapeutic index and it can be expressed as the ratio $LD_{50}/ED_{50}$. Compositions that exhibit large therapeutic indices are preferred. Suitable daily doses of the active compounds of the invention in therapeutic treatment of humans are about 0.01-10 mg/kg body-weight on peroral administration and 0.001-10 mg/kg body-weight on parenteral administration. For adults, suitable daily doses are within the range from about 0.01-2000 mg/kg body-weight, preferably from 0.1-1000 mg/kg body-weight, preferably from 1-100 mg/kg and these may be administered as single or divided doses, and in addition, the upper limit can also be exceeded when this is found to be indicated. Such dosage will be adjusted to the individual requirements in each case including the specific compound(s) being administered, the route of administration, the condition being treated, as well as the patient being treated.

Most preferably, compositions for use in the method of the present invention may comprise a therapeutically effective amount of compounds of formula (I) or (II) as described above, preferably chlorzoxazone or acetazolamide is of the range of 500 mg/day to 3 g/day with a frequency ranging from 2 to 4 times per day. Most preferably, such amount may be around 750 mg/day, 1.5 g/day, 2.25 g/day, or 3 g/day at a frequency of 3 or 4 times per day.

Treatment duration can be short-term, e.g., several weeks (for example 8-14 weeks), or long-term until the attending physician deems further administration no longer is necessary. The compounds can also be administered as depot preparations (implants, slow-release formulations, etc.) weekly, monthly or at even longer intervals. In such cases the dosage will be much higher than the daily one and may be adapted to the administration form, the body weight and the concrete indication. The appropriate dosage can be determined by conducting conventional model tests, preferably animal models. In general, in the case of oral or parenteral administration to adult humans weighing approximately 70 kg, a daily dosage of about 10 mg to about 10.000 mg, preferably from about 200 mg to about 1 mg, should be appropriate, although the upper limit may be exceeded when indicated.

Compositions for use in the method of the present invention may further comprise drugs which are conventionally used for the treatment of Fragile X Syndrome (FXS), Angelman syndrome, Williams-Beuren syndrome, Autism spectrum disorders (ASDs), hyperacusis, Smith-Magenis syndrome, Prader-Willi syndrome, 7q11.23 duplication syndrome, and cri-du-chat syndrome in combination with chlorzoxazone or acetazolamide. The drugs may be administered to a subject before, concomitantly, sequentially or after administration of chlorzoxazone or the acetazolamide.

Said combinations may further comprise medications which are conventionally used for easing the symptoms of these neuropsychiatric pathologies.

Typically, these medications may include antipsychotics for aggression or self-harming behaviour, mood stabilizers, antidepressants, anticonvulsants or antiepileptics, anxiolytics, psycho-stimulants to promote or increase wakefulness, alertness, physical activity, enhance cognition, learning or diminish fatigue, beta-adrenergic blockers, selective serotonin reuptake inhibitors (SSRIs) for depression and anxiety, non-SSRI antidepressants, melatonin for sleeping problems, cannabidiol for movement disorders, anxiety or cognitive dysfunction, and opioids.

Antipsychotics and mood stabilizers may include for example risperidone, lithium, lithium salt, lithium carbonate, procyclidine, and aripiprazole.

Anti-anxiety medications may include tiagabine, benzodiazepines, 2-methyl-6-(phenylethynyl)pyridine (MPEP); 2-chloro-4-((2,5-dimethyl-1-(4-(trifluoromethoxy)phenyl)-1H-imidazol-4-yl)ethynyl)pyridine (CTEP); Antiepileptics or anti-seizure medications may include carbamazepine, valproic acid, sodium valproate or divalproex lamotrigine, gabapentin, topiramate, tiagabine, vigabatrin, primidone, phenytoin.

Anti-depressant may include for example Group I mGluR antagonist, a muscarinic M1 antagonist, α2-adrenergic agonist, phenobarbital, L-acetylcarnitine, venlafaxine, nefazodone, fluoxetine, sertraline, citalopram, paroxetine, fluvoxamine, quetiapine, olanzapine, rolipram and trazodone.

Psychostimulant may include for example amantadine, bupropion, atomoxetine, modafinil, caffeine, methylphenidate, nicotine, allopregnanolone, pseudoephedrine, amphetamine, dextroamphetamine or derivatives thereof.

Conventional medications for ADHD such as methylphenidate, guanfacine and clonidine may be also combined with the compounds and compositions of the present invention.

Chlorzoxazone or acetazolamide may also be used in combination with therapeutic agents which have been tested for treating FXS, ASD, and/or Angelman syndrome, including for example a metabotropic glutamate receptor 5 antagonist (mGluR5 antagonist), the drug fenobam (or NPL2009) as tested in clinical trial NCT01806415; the drug AFQ056 (Jacquemont et al., Sci. Transl. Med., 2011 Jan. 5; 3-64) as tested in clinical trials NCT02920892, NCT01482143, NCT01253629, NCT01433354, NCT01357239, NCT01348087; the drug OV101 or gaboxadol as tested in clinical trial NCT03697161; the drug STX209 as tested in clinical trial NCT01013480, NCT01282268, NCT00788073; the drug acamprosate as tested in clinical trial NCT01911455; the drug ZYN002 as tested in clinical trial NCT03802799; the drug metadoxine or MG01CI as tested in clinical trial NCT02126995; the drug arbaclofen (or 209FX303) as tested in clinical trial NCT01282268 and NCT01555333; the drug minocycline, or the combination of minocycline/lovastatin as tested in clinical trial NCT02680379; the drug sertraline as tested in clinical trial NCT01474746; the drug as BPN14770 tested in clinical trial NCT03569631; the drug as ganaxolone as tested in clinical trial NCT01725152; the drug STX107 as tested in clinical trial NCT01325740; the drug basimglurant or RO4917523 as tested in clinical trial NCT01517698; the drug NNZ-2566 or trofinetide as tested in clinical trial NCT02715115; dietary supplement combination SXF-TRA152 (vitamins E and C) as tested in clinical trial NCT01329770; the drug AZD7325 as tested in clinical trial NCT03140813; and the drug ampakine or CX516 as tested in clinical trial NCT00054730.

Chlorzoxazone or acetazolamide may also be used in combinations with therapeutic agents which have been tested for treating Prader-Willi syndrome including for example the drug oxytocin as tested in clinical trials NCT02013258 and NCT03114371; the diazoxide choline as tested in clinical trial NCT03714373; cannabidiol as tested in clinical trials NCT02844933; the drug eutropin as tested in clinical trial NCT02204163; the drug anastrozole as tested in clinical trial NCT01520467; the combination of tesofensine and metoprolol as tested in clinical trial NCT03149445, and topiramate as tested in clinical trial NCT02810483.

EXAMPLES

Example 1: Clinical Trial to Assess Pharmacokinetics and Efficacy of the Chlorzoxazone for Treating or Reducing Symptoms of Cognitive Disorder, Behavioural Disorder, and Sensory Hyperexcitability Including Increased Sensitivity to Certain Frequencies and Ranges of Sound Intensity Levels in Adult FXS Patients This is a clinical phase IIa monocentric open label in adults.

20 Male adult patients (between 18 and 50 years old) having more than 200 CGG repeats within the FMR1 gene and an IQ score less than 80 are recruited.

Primary objective of this study is to assess the effects of chlorzoxazone on the behaviour of FXS adult patients based on the (Aberrant Behavior Check list-Community) ABC-C score which has been validated for neurological disorders of FXS patients.

Secondary objectives are to (i) assess the effects of chlorzoxazone comparative to the baseline of behavioural troubles measured with ABC-C score in terms of irritability, hyperreactivity, lethargy/social withdrawal, stereotypical behaviour and inappropriate language; (ii) assess the effects of chlorzoxazone on adaptive behaviour using Vineland; (iii) assess the effects of chlorzoxazone on sensory hyperexcitability as measured via electrodermal response or via the Acoustic startle response; and (iv) assess the tolerability of various dosages of chlorzoxazone.

Various dosages of chlorzoxazone are orally administered in the form of tablets 3 times per day (morning/noon/evening) during a 6-month period as described in the following Table 1:

TABLE 1

| Phase of treatment | Duration of each phase | % of the optimal dosage | Doses per day |
|---|---|---|---|
| Phase 1 | 1 month | 25% of the optimal dosage | 250 mg 3 times/day 750 mg total/day |
| Phase 2 | 2 months | 50% of the optimal dosage | 500 mg 3 times/day 1500 mg total/day |
| Phase 3 | 1 month | 75% of the optimal dosage | 750 mg 3 times/day 2250 mg total/day |
| Phase 4 | 2 months | 100% of the optimal dosage | 1000 mg 3 times/day 3000 mg total/day |

Any changes and effects of chlorzoxazone compared to the baseline are assessed primarily by the ABC-C score.

Other secondary criteria include:

any behavioural changes compared to baseline according to the ABC-C score;

any changes compared to sub-scales of ABC-C score including irritability, social withdrawal, stereotypical behaviour and inappropriate language;

the proportion of patients having a clinical response as defined by a reduction of 25% of the ABC-C score compared to the baseline;

the change of global symptoms of FXS as assessed by CGI-I (Clinical Global Impression-Improvement) which comprises a scale from 1 to 7, wherein 1 corresponds to a very good improvement, 4 corresponds to the absence of change and 7 corresponds to a negative change;

the change of the adaptive behaviour based on Vineland as compared to the baseline;

the proportion of patients having an improvement of the sensory hyperexcitability as measured by electrodermal response or Acoustic startle response;

the clinical tolerability monitored by physical signs: ECG (PR, QT, and rhythm disorder) and the monitoring of vital and biological signs the compliance of the treatment.

The total duration of the study is 52 weeks with a recruitment stage of 24 weeks, and a follow-up of 28 weeks total: 24 weeks of treatment and 4 weeks post-treatment.

Full-Scale IQ Test:

The assessment of the cognitive and mental development is assessed by the measure of the Full-Scale IQ using the Wechsler Adult Intelligence Scale or WAIS-IV (as released in 2008). The total IQ is obtained based on four index scores with the 10 core subtests yielding scaled scores that sum to derive the Full-Scale IQ. The four index scores are as follows:

Verbal Comprehension Index (VCI)

Perceptual Reasoning Index (PRI)

Working Memory Index (WMI)

Processing Speed Index (PSI)

Patients having a Full-Scale IQ of less than 80 are recruited.

Aberrant Behavior Check List-Community Test or ABC-C Test

This is a rating scale that measures the severity of a range of problem behaviours commonly observed in individuals having ID who live in communities. A version of the ABC-C test has been adapted to FXS (FXS-ABC-C test) with a focus on 6 fields: irritability, lethargy, social withdrawal, inappropriate language, hyperactivity and stereotypical behaviour.

Clinical Global Impression (CGI) Criteria

The CGI rating scales are measures of symptoms severity, treatment response and efficacy of the treatments. The clinical Global Impression-Severity scale (CGI-S) is a 7-point scale that requires the clinician to rate the severity of the patients illness at the time of assessment, relative to the clinician's past experience with patients who have the same diagnosis. The clinical Global Impression-Improvement (CGI-I) is a 7-point scale that requires the clinician to assess how much the patient's illness has improved or worsened relative to a baseline state at the beginning of the intervention.

Example 2: Dose-Response Study with Chlorzoxazone in WT Mice to Identify the Most Appropriate Dose to be Used for Mutant Animals Acute behavioural effects of various dosages of chlorzoxazone were measured on WT mice. The aim of this study was to identify the optimal dosage of the compounds and compositions of the present invention, i.e., the highest dose with no effect on WT mice and thus which can be used on mutant mice. The following doses of CHLOR were tested: 5, 10, and 20 mg/Kg i.p., administered 1 hour before the beginning of the tests. Tests of open field and acoustic startle were conducted in order to evaluate the pathologic phenotypes of neurodevelopmental pathologies in terms of hyperactivity and heightened sensitivity to sensory stimuli, particularly hyperacusis. Indeed, these two tests allow to detect behavioural abnormalities in mutant mice in a reliable and rapid manner minimizing the stress induced by behavioural testing. All mice were subjected to the open field test as a first step and then to the acoustic startle test after a 5 min break.

Example 2.1: Experimental Subjects

Adult (12 weeks_old) B6 (C57BL/6J) male mice were purchased from Janvier (Le Genest-Saint-Isle, France), housed in groups of 5 individuals, and left undisturbed for three weeks before being used for testing. All animals were housed in polycarbonate standard cages (33×15×14 cm in size; Tecniplast, Limonest, France), provided with litter (SAFE, Augy, France) and a stainless-steel wired lid. Food (SAFE, Augy, France) and water were provided ad libitum. The animals were maintained in a temperature (22° C.) and humidity (55%) controlled vivarium, under a 12:12 hr light-dark cycle (lights on at 7 a.m.). All experimental procedures were in accordance with the European Communities Council Directive of 24 Nov. 1986 (86/609/EEC) and local French legislation.

Example 2.2: Drug Preparation

All injectable solutions were freshly prepared on each experimental day. CHLOR (Sigma Aldrich, France) was dissolved in saline solution containing 1.25% DMSO (Sigma Aldrich, France) and 1.25% Tween80 (Sigma Aldrich, France). The same solution without drugs was used for the VEH control group. The following doses of CHLOR were tested: 5, 10, and 20 mg/Kg i.p., 1 hour before the beginning of the first test.

Example 2.3: Behavioural Tests

Open Field Test

The open field test is conventionally used to test the locomotor and exploratory activities of the laboratory mice. The test comprised 4 arenas in opaque plastics having a size of 42×26×15 cm. Each mouse was placed in the centre of the arena and let free to explore for a duration of 5 minutes. Mouse movements were automatically recorded with a camera placed above the arenas and evaluated with Ethovision (version 11, Noldus Technology, Wageningen, NL) to analyze the total distance covered by the mice.

Acoustic Startle Test

This test uses acoustic stimuli of weak intensity in order to detect an hypersensitivity to sensory stimuli. The apparatus consisted of four acoustic startle chambers for mice (SR-LAB, San Diego Instruments, San Diego, CA, USA). Each comprised a non-restrictive cylindrical enclosure made of clear Plexiglas attached horizontally on a mobile platform, which was in turn resting on a solid base inside a sound-attenuated isolation cubicle. A high-frequency loudspeaker mounted directly above the animal enclosure inside each cubicle produced a continuous background noise of 66 dBA and various acoustic stimuli in the form of white noise. Vibrations of the Plexiglas enclosure caused by the whole-body startle response of the animal were converted into analogue signals by a piezoelectric unit attached to the platform. These signals were digitized and stored by a computer. The sensitivity of the stabilimeter was routinely calibrated to ensure consistency between chambers and across sessions.

A session began when the animals were placed into the Plexiglas enclosure. They were acclimatized to the apparatus for 5 minutes before the first trial began. Mice were then presented with pulses of white sound of 20 ms duration and varying intensity: +6, +12 +18 and +24 dB over background levels (namely 72, 78, 84 and 90 dB). Each intensity was presented 8 times, in a randomized order with variable intervals (10 sec to 20 sec) between the onset of each pulse. Mice were habituated to the boxes in the absence of acoustic stimuli 24 hs prior to testing to reduce stress. A total of 130 readings of the whole-body startle response were taken at 0.5-ms intervals (i.e., spanning across 65 ms), starting at the onset of the pulse stimulus. The average amplitude (in mV) over the 65 ms was used to determine the stimulus reactivity and further averaged across trials. A natural logarithmic transformation was applied in order to fulfill the normality criteria requested by parametric ANOVA.

All behavioural tests were carried out during the light phase of the cycle. Mice were habituated to the experimental room prior to all behavioural tests, being individually housed in standard polycarbonate cages provided with saw-dust, food, and water bottles and left undisturbed for at least 10-15 min before testing began.

Example 2.4: Statistical Analysis

Data were analyzed with a 4-way ANOVA using treatment as the between-subject factor and adding stimulus intensity as the within-subject factor for the acoustic startle data. Post-hoc comparisons were performed using Fisher's Least Significant Difference (LSD). All analyzes were carried out using Statview and PASW Statistics 18.

Example 2.5: Results

Figure 2:
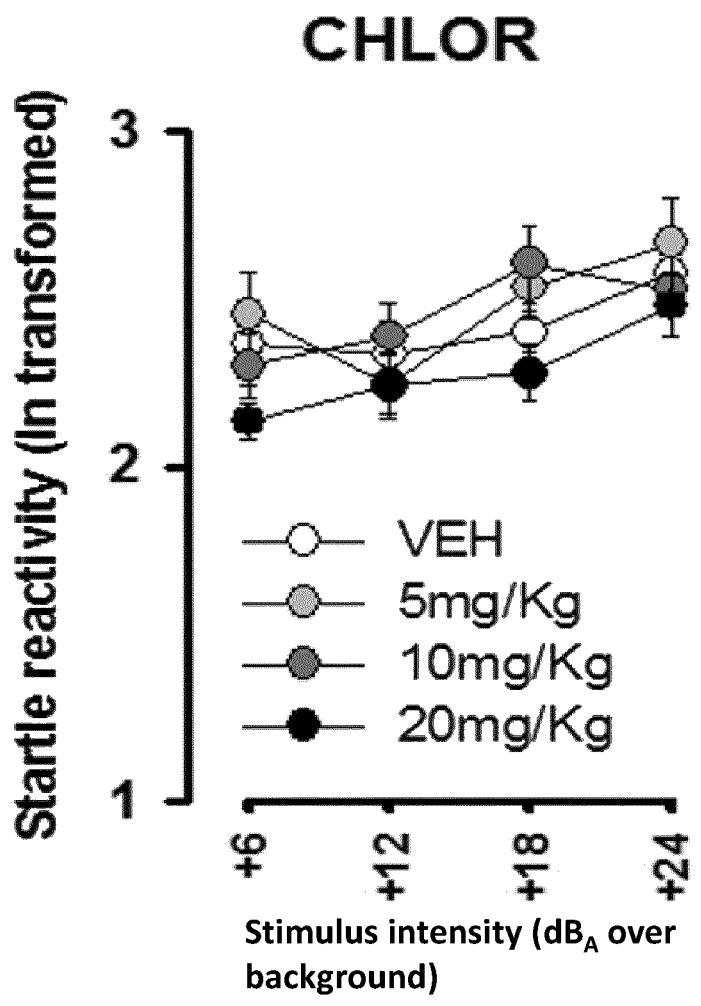
FIG. 2: is a graph showing the sensory response of WT mice in the acoustic startle test (n=9-10) after acute treatment with various doses of chlorzoxazone (CHLOR): 5 mg/kg, 10 mg/kg and 20 mg/kg. Stimulus intensities are expressed over (+) a background of 66 dB.

As showed in FIG. 1, treatment with chlorzoxazone clearly modified the locomotor activity of WT mice in the open field starting at a dose of 10 mg/kg. However, no changes have been observed at the same dosage in the acoustic startle test (FIG. 2). The 5 mg/kg dose was therefore determined to be the highest one having no effect on WT mice and was used for the subsequent studies on mutant mice.

Example 3: Preliminary Evaluation of the Acute Behavioural Effects of Chlorzoxazone in Fmr1-KO Mice Based on the results obtained in Example 2, Chlorzoxazone at a dose of 5 mg/kg was thus administered to Fmr1-KO mice and to WT controls and their behaviours were analyzed with the open field and acoustic startle tests to obtain preliminary evidence of the acute behavioural effects of CHLOR.

Example 3.1: Experimental Subjects

Subjects were adult (6 months old) male Fmr1-KO and their wild-type littermates, bred in our animal facility of Bordeaux University. C57BL/6JFmr1tm1Cgr/Nwu (B6) breeders were originally obtained from Neuromice.org (Northwestern University). Breeding trios were formed by mating two heterozygous Fmr1 females with a wild-type C57BL/6J male purchased from Janvier (Le Genest St Isle, France). After 2 weeks the sire was removed, and the females were single caged and left undisturbed until weaning of the pups. Mice were weaned at 21 days of age and group-housed with their same-sex littermates (3-5/cage). On the same day, tail samples were collected for DNA extraction and subsequent PCR assessment of the genotypes as previously described (Dutch-Belgian Fragile X Consortium, 1994). Only litters including males of both genotypes (WT and KO) were used for experiments.

All animals were group-housed in polycarbonate standard cages (33×15×14 cm in size; Tecniplast, Limonest, France), provided with litter (SAFE, Augy, France) and a stainless-steel wired lid. Food (SAFE, Augy, France) and water were provided ad libitum. The animals were maintained in a temperature (22° C.) and humidity (55%) controlled vivarium, under a 12:12 hr light—dark cycle (lights on at 7 a.m.). All experimental procedures were in accordance with the European Communities Council Directive of 24 Nov. 1986 (86/609/EEC) and local French legislation.

Example 3.2: Drug Preparation

All injectable solutions were freshly prepared on the experimental day, as described for Example 2.2. Briefly, CHLOR was dissolved in saline solution containing 1.25% DMSO (and 1.25% Tween80 and the same solution without drugs was used for the VEH control group.

Example 3.3: Behavioural Tests

A single injection of the solvent or of the composition of the invention with chlorzoxazone has been administered to Fmr1-KO and WT mice 1 hour before the beginning of the first behavioural test, i.e., the open field followed by the acoustic startle test. Open field and acoustic startle were assessed following the same procedures described in Example 2.

Example 3.4: Statistical Analysis

All data were analyzed with ANOVA using treatment and genotype as the between-subject factors and adding stimulus intensity as the within-subject factor for the acoustic startle data. Post-hoc comparisons were performed when a significant interaction genotype x treatment was found using Tukey's-Kramer test. Otherwise, separate oneway ANOVAs in each treatment group with genotype as the between subject factor were conducted, if appropriate. All analyzes were carried out using Statview and PASW Statistics 18.

Example 3.5: Results

Figure 3:
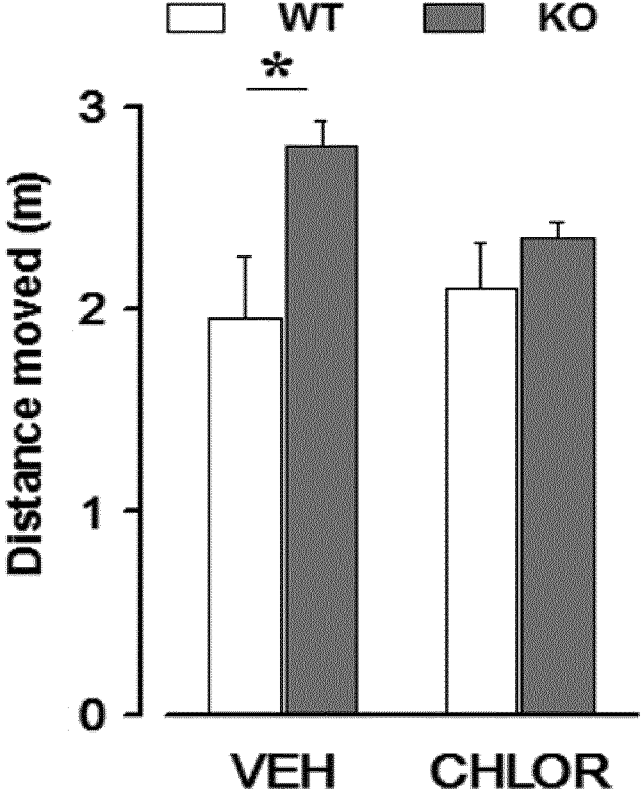
FIG. 3: is a graph showing the locomotor activity of Fmr1 deficient mice (KO) and their WT littermates in an open field test further acute administration of 5 mg/kg of chlorzoxazone (CHLOR) (n=5-8; *=p<0.05).

The results show that KO mice were more active in the open field test than WT mice. Genotype effect: $F_{(1.20)}=8.99$; $p<0.01$; FIG. 3 and this effect disappeared after the treatment with chlorzoxazone (genotype effect in mice VEH: $F_{(1.10)}=8.29$; $p<0.01$; in mice CHLOR: $F_{(1.10)}=1.3$; ns; See FIG. 3).

Figure 4:
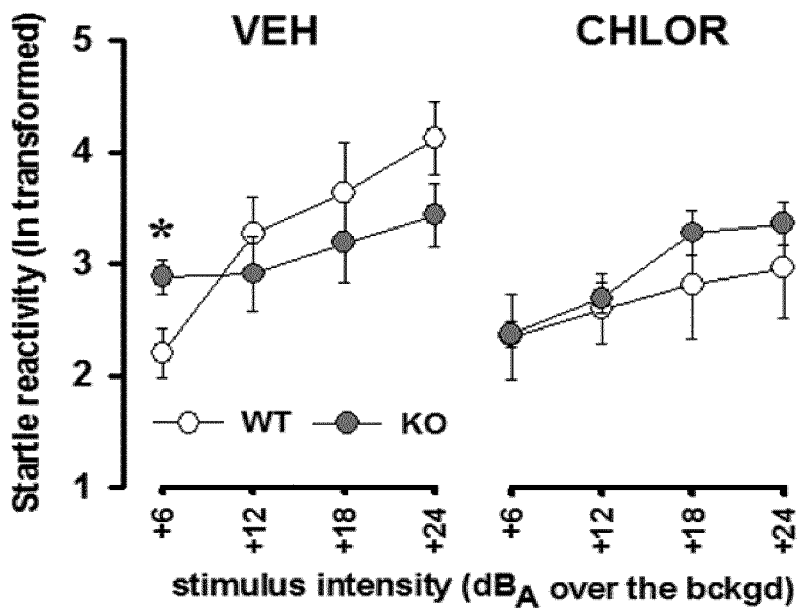
FIG. 4: is a graph showing the sensory response of Fmr1 deficient mice (KO) and their WT littermates in the acoustic startle test after acute administration of 5 mg/kg of chlorzoxazone (CHLOR) (n=5-8; *=p<0.05). Stimulus intensities are expressed over (+) a background of 66 dB.

In the acoustic startle test, KO mice in the condition VEH presented a higher reactivity to a sensory stimulus, particularly to a stimulus of the weakest intensity. This effect was eliminated with chlorzoxazone ($F_{(3.63)}=4.02$, $p<0.05$; post-hoc: WT-VEH versus KO-VEH, $p<0.05$; See FIG. 4).

These results clearly showed the efficacy of the acute administration of chlorzoxazone on both behavioural phenotypes of FXS in its animal model (Fmr1-KO mice). These data also confirmed the superior therapeutic efficacy of the chlorzoxazone for the treatment of FXS and related synaptopathies, such as Williams-Beuren syndrome and Down's syndrome.

Example 4: Dose-Response Study with Acetazolamide in WT Mice to Identify the Most Appropriate Dose to be Used for Mutant Animals Acute behavioural effects of various dosages of acetazolamide were measured on WT mice. The objective of this study was to evaluate the optimal dose which can be administered during subsequent studies on KO mice, i.e., the highest dose having no effect in WT mice. The following doses have been used: 10, 20, and 40 mg/kg i.p. administered 1 hour before the beginning of the tests.

Example 4.1: Experimental Subjects

Adult (12 weeks_old) B6 (C57BL/6J) male mice were used; they were obtained, housed and maintained according to the same procedures described in detail in Example 2.

Example 4.2: Drug Preparation

All injectable solutions were freshly prepared on the experimental day, as described for example 2 and 3. Briefly, ACEZ was dissolved in saline solution containing 1.25% DMSO (and 1.25% Tween80 and the same solution without drugs was used for the VEH control group.

Example 4.3: Behavioural Tests

A single injection of the solvent or of the one of the doses of acetazolamide (10, 20, and 40 mg/kg)has been administered to WT mice 1 hour before the beginning of the first behavioural test, i.e., the open field followed by the acoustic startle test. Open field and acoustic startle tests were conducted following the same procedures described in Example 2.

Example 4.4: Statistical Analysis

Statistical analyzes were carried out as previously described for example 2. Briefly, data were analyzed with a 4-way ANOVA using treatment as the between-subject factor and adding stimulus intensity as the within-subject factor for the acoustic startle data. Post-hoc comparisons were performed using Fisher's Least Significant Difference (LSD).

Example 4.5: Results

Figure 5:
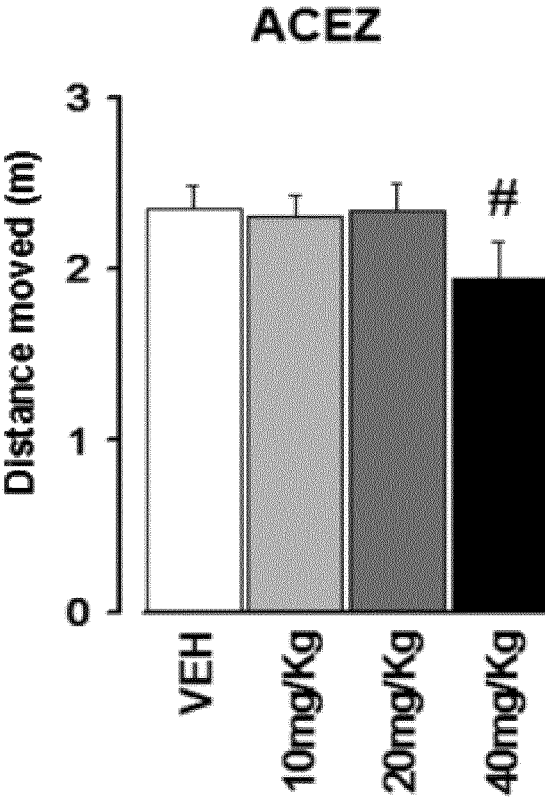
FIG. 5: is a graph showing the locomotor activity of WT mice in an open field test further acute administration of various doses of acetazolamide (ACEZ): 10 mg/kg, 20 mg/kg and 40 mg/kg (n=9-10; #=p=0.08 versus VEH and 40 mg/kg).
Figure 6:
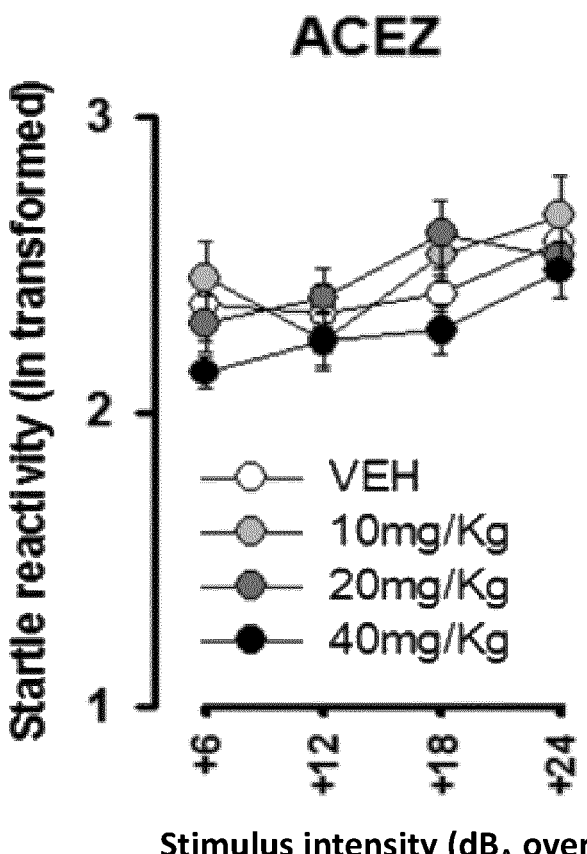
FIG. 6: is a graph showing the sensory response of WT mice in the acoustic startle test after acute administration of various doses of acetazolamide (ACEZ): 10 mg/kg, 20 mg/kg and 40 mg/kg (n=9-10). Stimulus intensities are expressed over (+) a background of 66 dB.

The highest dose of acetazolamide (40 mg/kg) seemed to induce a reduction in the locomotion in the open field (FIG. 5). However, such effect was not statistically significant. No effects were observed during the acoustic startle test for which only a significant effect of the stimulus has been observed (FIG. 6).

Example 5: Preliminary Evaluation of the Acute Behavioural Effects of Acetazolamide in Fmr1-KO Mice Based on the results of Example 4, the dose of 20 mg/kg of acetazolamide has been selected since it was the highest dosage of acetazolamide having clearly no effect on WT mice. A single injection i.p. of the solvent or of the dose of 20 mg/kg of acetazolamide was thus administered to Fmr1-KO mice and WT mice and their behaviours have been analyzed in the open field and acoustic startle tests as previously done in the example 3. The characteristics of experimental subjects, drug preparation, procedures for behavioural testing and statistical analysis were the same described in example 3.

Figure 7:
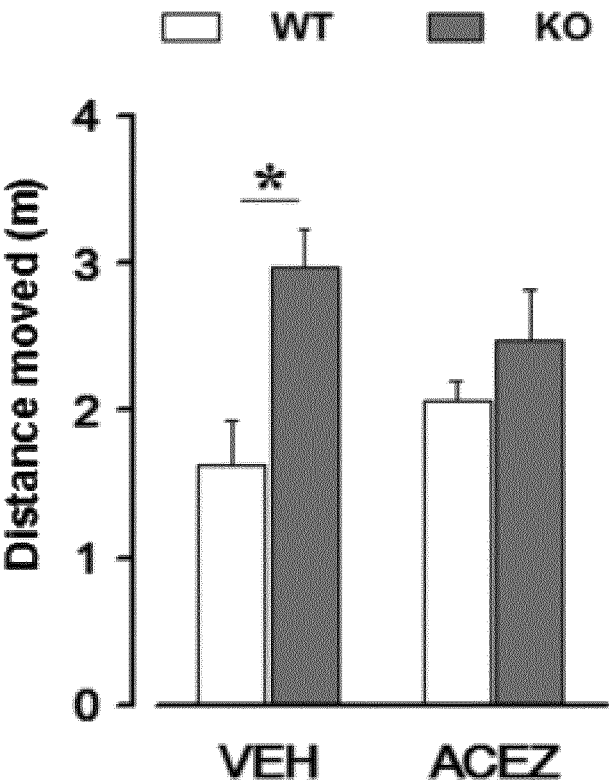
FIG. 7: is a graph showing the locomotor activity of Fmr1 deficient mice (KO) and their WT littermates in an open field test further acute administration of 20 mg/kg of acetazolamide (ACEZ) (n=5-8; *=p<0.05).

The results show that KO mice were more active in the open field when compared to WT mice. Genotype effect: $F_{(1.20)}=8.99$, $p<0.01$ (FIG. 7) and this effect disappeared after the treatment with acetazolamide (genotype effect in mice VEH: $F_{(1.11)}=11.25$; $p<0.01$; in mice ACEZ: $F_{(1.10)}=0.8$; ns; See FIG. 7).

Figure 8:
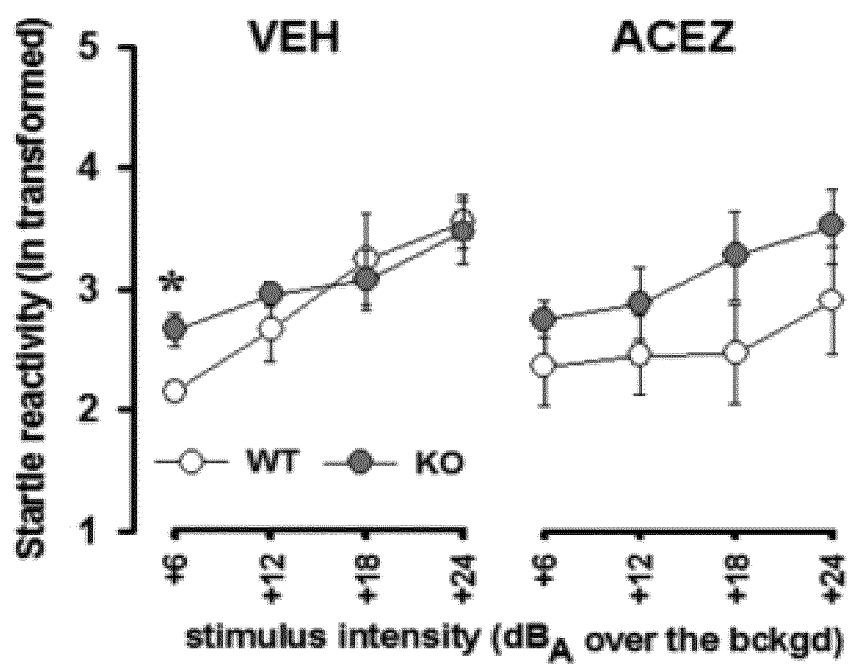
FIG. 8: is a graph showing the sensory response of Fmr1 deficient mice (KO) and their WT littermates in the acoustic startle test after acute administration of 20 mg/kg of acetazolamide (ACEZ) (n=5-8; *=p<0.05). Stimulus intensities are expressed over (+) a background of 66 dB.

In the acoustic startle test, KO mice in conditions VEH presented a higher reactivity to a sensory stimulus, particularly to a stimulus of 1 the weakest intensity. This effect is eliminated with acetazolamide (ACEZ); Effect of genotype in VEH mice: $F_{(1.11)}=8.08$, $p<0.05$; effect of in ACEZ mice: $F_{(1.10)}=1.46$, ns; See FIG. 8).

These results clearly showed the efficacy of the administration of acetazolamide on both behavioural phenotypes of FXS in one animal model (Fmr1-KO mice). These data also confirmed the superior therapeutic efficacy of the acetazolamide for the treatment of FXS and related synaptopathies, such as Williams-Beuren syndrome and Down's syndrome.

Example 6: Extensive Evaluation of the
Therapeutic Effects of Chlorzoxazone (CHLOR) in
Animal Models of Fragile X Syndrome We conducted a series of studies on mutant mice to obtain further preclinical evidence for therapeutic effects of CHLOR in mouse models of FXS. These studies included the evaluation of chronic and acute effects of CHLOR on multiple behaviours relevant to FXS, and comparison with other treatments proposed for FXS, as well the assessment of non-behavioural effects and the inclusion of multiple genetic models of FXS.

Example 6.1: Experimental Subjects

Subjects of most of the studies described here were adult (5-6 months old) male Fmr1-KO and their wild-type littermates, on B6 background (Dutch-Belgian Fragile X Consortium, 1994), bred and maintained in our animal facility of Bordeaux University as previously described in details for Example 3.

NMRI female mice (12±1 weeks old) purchased from Janvier (Le Genest St Isle, France) were used as social stimuli during the social interaction test. This strain has been selected for its high level of sociability and was previously employed in several social studies from our group on Fmr1-KO mice. Mice were group-housed (4-5/cage) and left undisturbed upon arrival at least one week before the social interaction test.

All animals were housed in polycarbonate standard cages (33×15×14 cm in size; Tecniplast, Limonest, France), provided with litter (SAFE, Augy, France) and a stainless-steel wired lid. Food (SAFE, Augy, France) and water were provided ad libitum. The animals were maintained in a temperature (22° C.) and humidity (55%) controlled vivarium, under a 12:12 hr light-dark cycle (lights on at 7 a.m.). All experimental procedures were in accordance with the European Communities Council Directive of 24 Nov. 1986 (86/609/EEC) and local French legislation.

Example 6.2: Behavioural Tests

To evaluate the therapeutic potential of CHLOR we have chosen behavioural tests that are currently used to evaluate FXS- and autistic-like behaviours. These include hyperactivity (the open field test), spatial memory (the Y maze test for spontaneous alternation), social deficits (direct social interaction test), repetitive behaviours (self-grooming test in a novel environment), and sensory hyper-responsiveness (acoustic startle test).

The tests chosen have the following crucial advantages. They first allowing detecting behavioural abnormalities of Fmr1-KO mice that have been repeatedly and consistently described across several studies. They also allow a rapid (because of the short duration and the possibility of testing multiple animals at the same time) and mostly automatic assessment of mouse behaviour. Furthermore, they require minimal manipulation and stress of the subjects, thus allowing repeated testing of the same mice (and reducing the number of subjects needed).

Open field test: this 5-min test was used to assess locomotor activity and exploration in laboratory mice, as described in details for the Example 2.

Spatial memory in the Y maze test for spontaneous alternation: Spatial memory was assessed in a grey, plastic Y-maze, as previously described. Briefly, during the first sample phase, access to the third novel arm was blocked by a door; mice were placed at the end of the start arm and allowed to freely explore the start and the other unblocked arm for 5 min before being returned to a waiting cage. After 2 min in the waiting cage, the test phase began: the door was removed; mice were placed at the end of the start arm and allowed to explore the entire maze for 2 min. Time spent in each arm of the maze was analyzed during both phases of the experiment as well as the distance traveled. Spontaneous alternation was assessed as follows: (Time spent in the novel arm/Time spent in all arms)×100.

Direct social interaction test: Social interaction was assessed in a 30×15×14 cm cage, covered by a flat metal grid and with approximately 3 cm of sawdust on the floor, where male subjects were previously isolated for one hour. An unfamiliar NMRI female (3 months-old), was then introduced into the testing cage and left there for 3 min. Stimulus females were housed in unisexual groups in a female-only animal room and were in the non-oestrous phase when tested (as assessed by the analysis of vaginal smears). Testing sessions were recorded, and videos analyzed with Observer XT (version 7, Noldus, The Netherlands). Time spent in affiliative behaviours of the male subject was evaluated, including sniffing the head and the snout of the partner, its anogenital region, or any other part of the body; allogrooming (grooming the partner) and traversing the partner's body by crawling over/under from one side to the other.

Self-grooming test in a novel environment: The apparatus consisted of an unfamiliar Plexiglas cage (30×15×14 cm), covered by a flat metal grid and with approximately 3 cm of sawdust on the floor. A camera was placed in front of the cage for videorecording. Mice were singly placed in the apparatus and allowed exploring for 20 minutes. Total time spent grooming was scored with Observer XT (version 7, Noldus, The Netherlands) by an observer who was blind to animals' genotype and treatment.

Acoustic startle test: This test used a particular protocol involving low intensity stimuli that has been used so far only in Fmr1-KO mice where it has allowed detecting the sensory-hyper responsiveness of FX mice. The apparatus and procedures were the same previously described for Example 2.

Example 6.3: Drug Preparation

All injectable solutions were freshly prepared on each experimental day, as described in Examples 2 and 3. CHLOR (Sigma Aldrich, France) and MET (Sigma Aldrich, France) were dissolved in saline solution containing 1.25% DMSO (Sigma Aldrich, France) and 1.25% Tween80 (Sigma Aldrich, France). The same solution without drugs was used for the VEH control group.

Example 6.4: Statistical Analysis

All data were analyzed with ANOVA using treatment and genotype as the between-subject factors and adding stimulus intensity as the within-subject factor for the acoustic startle data. Post-hoc comparisons were performed when a significant interaction genotype x treatment was found using Tukey's-Kramer test. Otherwise, separate oneway ANOVAs in each treatment group with genotype as the between subject factor were conducted, if appropriate. Data from the Y maze were also analyzed using a one-sample t-test to evaluate the significant difference from the chance level, as done in previous studies. All analyzes were carried out using Statview and PASW Statistics 18.

Example 6.5: Study 1- Comparing CHLOR Versus Metformin: Chronic Effects in Fmr1-KO Mice Mice received a daily i.p. injection of VEH solution, CHLOR (5 mg/kg) or MET (200 mg/kg) for 10 days, following the experimental protocol previously described in a study showing behavioural effects of MET in mice. Behavioural tests were conducted 24 hs after the last injection, in order to avoid acute effects.

Figure 9:
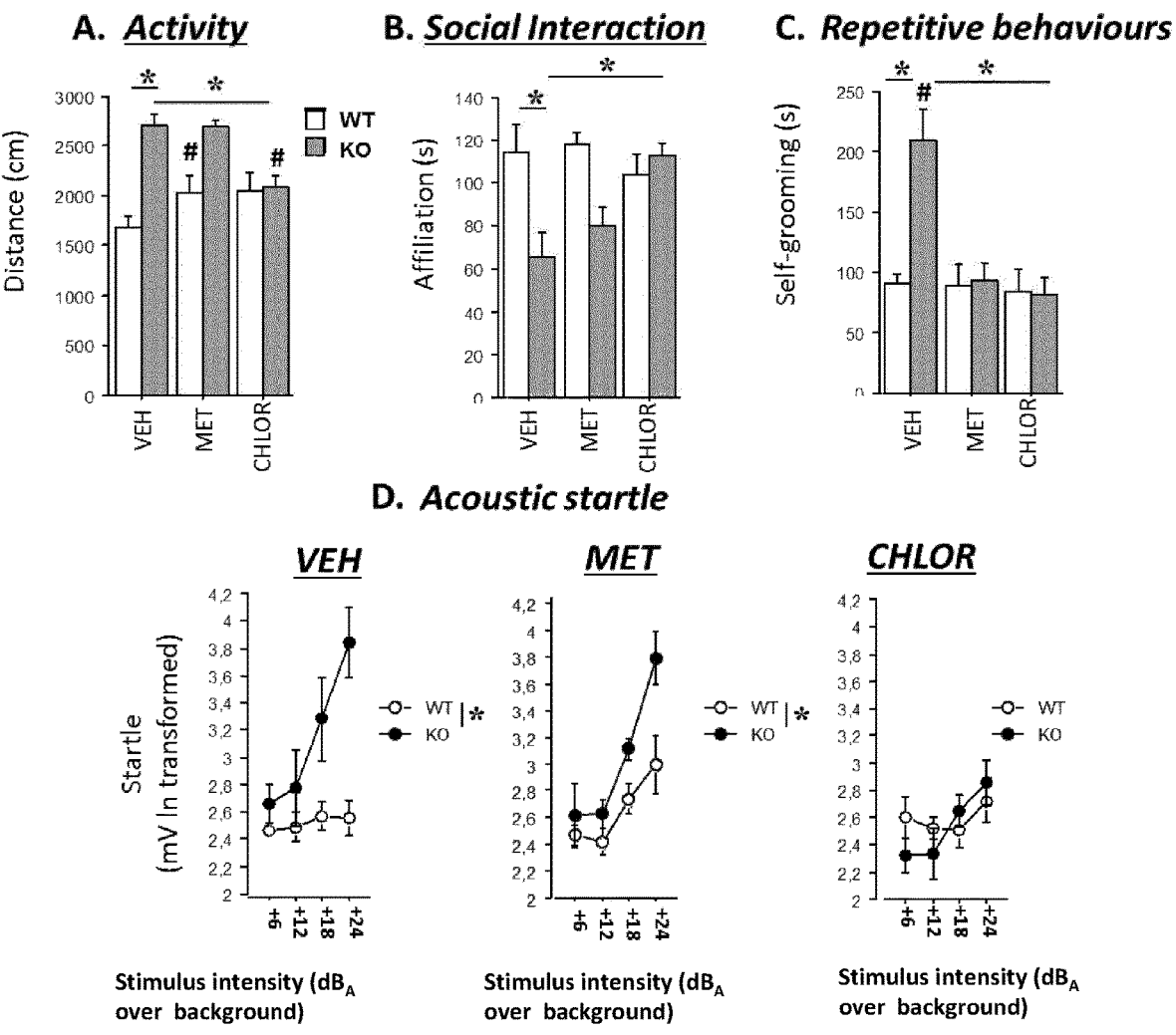
FIGS. 9A-D: are graphs showing the chronic effects of chlorzoxazone (CHLOR; 5 mg/kg) versus Metformin (MET, 200 mg/kg) in Fmr1 deficient mice (KO) and their WT littermates: Behavioural tests were conducted after 10 days of i.p. injections (with a 24 hs interval from the last injection) and they included open field test for locomotor activity (A), direct social interaction with a WT female (B), evaluation of self-grooming in a novel cage (C) and acoustic startle response test (D). n=6-8; *=p<0.05; #=versus KO-MET. Stimulus intensities are expressed over (+) a background of 66 dB.

As expected, Fmr1-KO mice treated with VEH showed hyperactivity (FIG. 9A), and reduced social interaction (FIG. 9B); these abnormalities were not attenuated by MET administration, but were eliminated by CHLOR [interaction genotype x treatment, respectively: $F_{(2.34)}=7.05$, and $F_{(2.30)}=5.32$, p<0.01 and =0.01; post-hoc: KO-VEH versus WT-VEH, KO-CHLOR versus KO-VEH: p<0.05; for hyperactivity, also KO-MET versus WT-MET and KO-CHLOR: p<0.05]. Similarly, only CHLOR eliminated the exaggerated acoustic response of KO mice that was especially marked at the highest stimulus intensities; nonetheless, this acoustic abnormality seemed slightly less pronounced following MET treatment [FIG. 9D; interaction genotype x intensity: $F_{(3.102)}=9.41$, p<0.0001; interaction genotype x treatment $F_{(2.34)}=4.48$, p<0.05; genotype effects in separate ANOVAs: in VEH $F_{(1.11)}=10.03$, p<0.01; in MET $F_{(1.11)}=7.13$, p<0.05, in CHLOR, n.s.]

KO-VEH mice also spent more time performing self-grooming (FIG. 9C), that is considered an index of anxiety/repetitive behaviour and this abnormal phenotype was eliminated by both MET and CHLOR chronic administration [interaction genotype x treatment: $F_{(2.30)}=8.24$, p<0.01; post-hoc: KO-VEH versus WT-VEH, KO-CHLOR and KO-MET: p<0.05].

Figure 10:
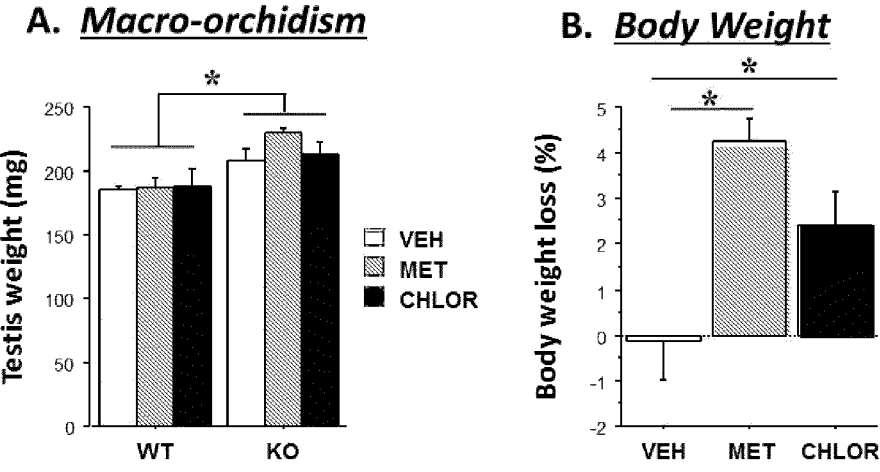
FIGS. 10A-B: are graphs showing the chronic non-behavioural effects of CHLOR (5 mg/kg) and MET (200 mg/kg) in Fmr1 deficient mice (KO) and their WT littermates: Testis weight (A) and body weight (B) were assessed after 10 days of i.p. injections. n=6-8; *=p<0.05.

To include potential non-behavioural effects (FIG. 10), we investigated whether chronic CHLOR or MET could rescue the macro-orchidism known to affect Fmr1-KO mice (as FXS patients). None of the treatments eliminated the enhanced testicular weight of Fmr1-KO mice (FIG. 10A, genotype effect $F_{(1.34)}=19.51$, p<0.0001; all other effects and interaction: n.s.). Body weight was slightly reduced after both CHLOR and MET chronic treatments, an effect that was equally observed in WT and KO mice (FIG. 10B, treatment effect on body weight loss: $F_{(2.34)}=10.25$, p<0.001; post-hoc: CHLOR and MET versus VEH: p<0.05).

Figure 11:
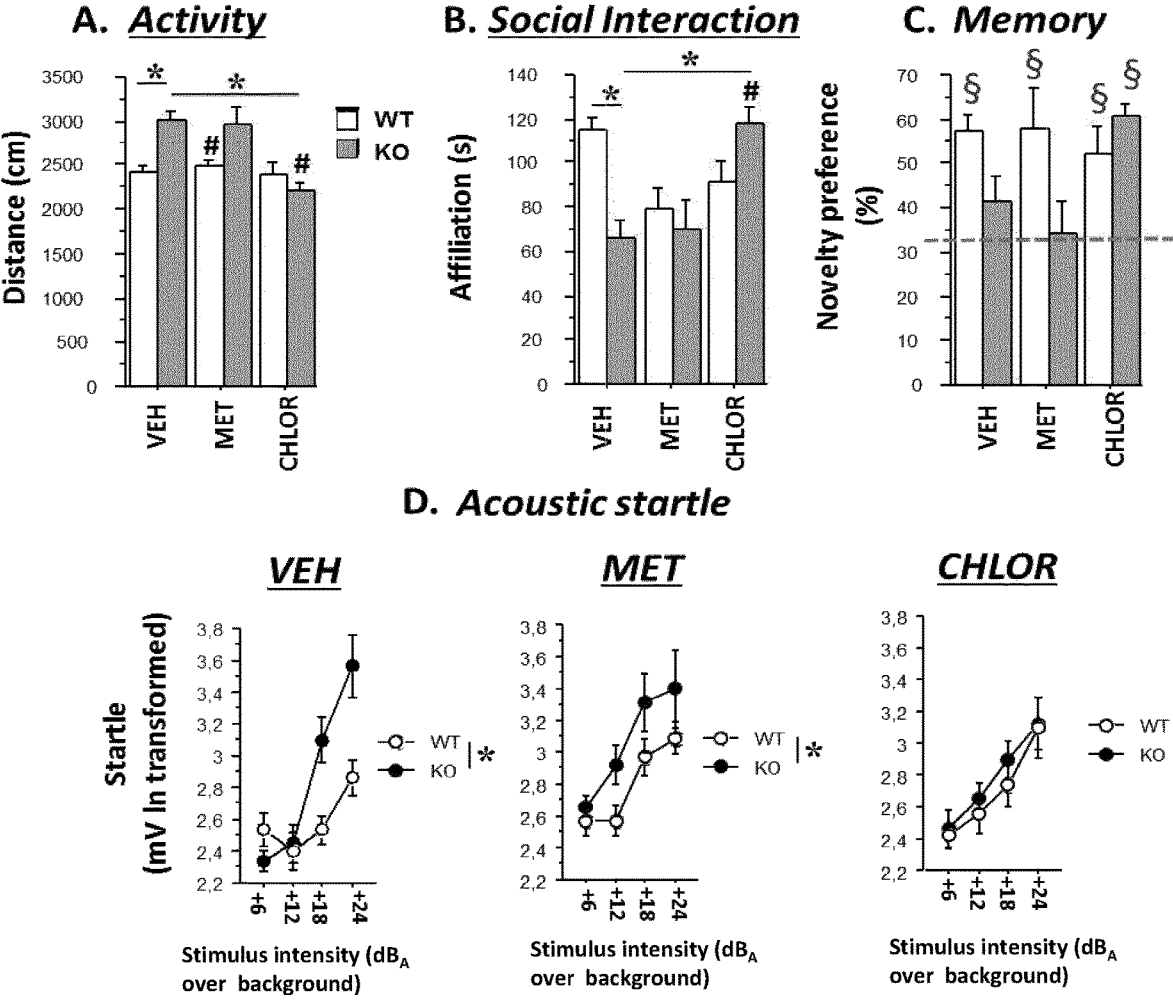
FIGS. 11A-D: are graphs showing the acute effects of chlorzoxazone (CHLOR; 5 mg/kg) versus Metformin (MET, 200 mg/kg) in Fmr1 deficient mice (KO) and their WT littermates: Behavioural tests were conducted 1 h after a single i.p. injection and they included open field test for locomotor activity (A), direct social interaction with a WT female (B), Y maze test for spatial memory (C) and acoustic startle response test (D). n=8-10; *=p<0.05; #=versus KO-MET, §=versus chance level. Stimulus intensities are expressed over (+) a background of 66 dB.

Example 6.6: Study 2: Comparing CHLOR Versus Metformin: Acute Effects in Fmr1-KO Mice Mice received a single i.p. injection of VEH solution, CHLOR (5 mg/kg) or MET (200 mg/kg). One hour after injection, animals were submitted to the open field test, social interaction test, Y maze test for spontaneous alternation and acoustic startle test. As expected, Fmr1-KO mice treated with VEH showed hyperactivity (FIG. 11A), and reduced social interaction (FIG. 11B); these abnormalities were not attenuated by acute MET administration, but were eliminated by CHLOR [interaction genotype x treatment, respectively: $F_{(2.53)}=6.13$, and $F_{(2.48)}=8.85$, both p<0.01; post-hoc: KO-VEH versus WT-VEH, KO-CHLOR versus KO-VEH and KO-MET: p<0.05; for hyperactivity, also WT-MET versus KO-MET: p<0.05]. CHLOR also restored spatial memory in the Y maze in Fmr1-KO mice (t-test, p<0.05, FIG. 11C), while KOs treated with MET showed a performance similar to those receiving VEH, i.e., not different from the chance level (t-test, n.s., FIG. 11C). Finally, Fmr1-KO mice treated with VEH displayed enhanced acoustic startle, especially at the highest stimulus intensities (FIG. 11D), and this effect was eliminated by acute CHLOR, but not MET [overall effects of genotype: $F_{(1.53)}=7.69$ p<0.01 and treatment $F_{(2.53)}=3.33$, p<0.05; interaction genotype x treatment x stimulus intensity: $F_{(6.159)}=2.09$, p=0.05; genotype effects in separate ANOVAs: in VEH $F_{(1.16)}=6.06$, p<0.05; in MET $F_{(1.19)}=5.66$, p<0.05, in CHLOR, n.s.].

Example 6.7: Study 3: Dose-Response of CHLOR Acute Effects in Fmr1-KO Mice

We then performed a dose-response study on the acute effects of CHLOR in Fmr1-KO mice. The aim of this study was to evaluate whether a dose lower than the one used so far, i.e., 5 mg/kg, could be sufficient to induce acute beneficial behavioural effects in Fmr1-KOs. The following doses of CHLOR were used: 1.25, 2.5 3.75, and 5 mg/kg corresponding to 25, 50, 75 and 100% of the original dose. A single i.p. injection of either the Vehicle or one of the CHLOR solutions was administered in Fmr1-KO mice and their WT littermates 1 hour before the beginning of behavioural testing. Hyperactivity in the open field and acoustic startle response were assessed as in previous studies.

Figure 12:
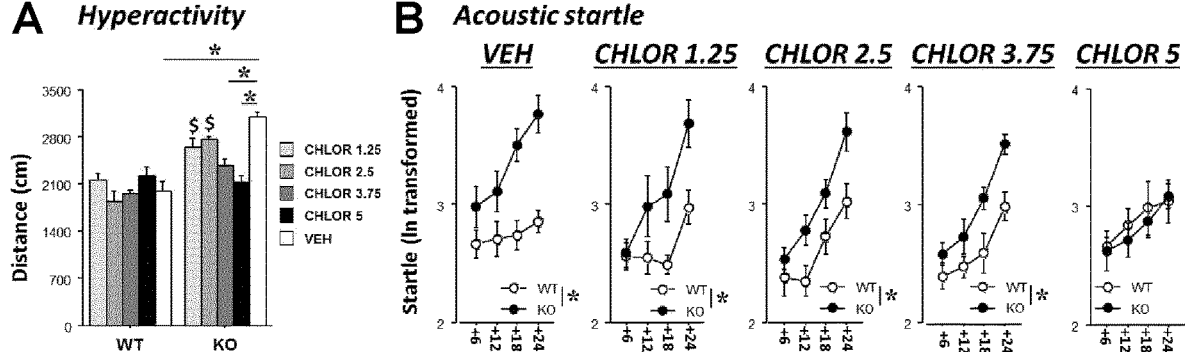
FIGS. 12A-B: are graphs showing the dose-response study on the acute effects of CHLOR in the open field (A) and acoustic startle (B) tests in Fmr1 deficient mice (KO) and their WT littermates. n=9-10; *=p<0.05. $ versus WT with same treatments: p<0.05. Doses are expressed as mg/kg; treatments were administered 1 hr before testing. Stimulus intensities are expressed over (+) a background of 66 dB.

A dose effect of CHLOR was found on hyperactivity of KO mice, the dose of 5 mg/kg being the most effective in reducing the hyper-locomotion of mutant animals, followed by the 3.75 mg/kg dose [FIG. 12A: interaction genotype x treatment on the distance moved: $F_{(4.68)}=10.08$, p<0.0001; post-hoc: KO-VEH versus WT-VEH and versus KO-CHLORS and KO-CHLOR3.75; KO-CHOR1.25 and KO-CHLOR2.5 versus WT with same treatments: p<0.05]. Similar results were observed on the acoustic startle, but only the highest dose of 5 mg/kg was able to fully rescue the acoustic hyper-responsiveness of KO mice [FIG. 12B: interaction genotype x treatment: $F_{(4.68)}=2.26$, p=0.07; interaction genotype x treatment x stimulus intensity: $F_{(12.204)}=1.67$, p=0.07; genotype effects in separate ANOVAs: in VEH $F_{(1.14)}=3.56$, p<0.01; in CHLOR1.25 $F_{(1.14)}=4.75$, p<0.05, in CHLOR2.5 $F_{(1.14)}=8.44$, p<0.05, in CHLOR3.75 $F_{(1.13)}=9.14$, p<0.05, in CHLORS n.s.].

Example 6.8: Study 4—Acute Effects of CHLOR in the Fmr1-KO Mouse Model of Second Generation (Fmr1-KO2 Mouse Line)

The Fmr1-KO mouse model we have used so far was engineered in 1994 (The Dutch-Belgian Fragile X Consortium, 1994) and is still the most widely used in the research on FXS and ASD for behavioural, molecular and electro-physiological studies. Nonetheless, another Fmr1-KO mouse line of the second generation is also available, differing from the original Fmr1 model because of the full absence not only of the FMRP protein, but also of related mRNAs. This model, known as Fmr1-KO2, is less widely used in neurobiological research and mostly for electro-physiological and molecular investigations. Indeed, when we have performed an extensive behavioural characterization of Fmr1-KO2 mice at adulthood, we detected a less varied ASD- and FXS-like phenotype compared to the first Fmr1-KO model. For example, we did not find hyperactivity and social deficits in KO2 mice, while exaggerated acoustic startle response was confirmed as a robust behavioural alteration also of these mutants. Hence, we assessed whether a single injection of the dose of 5 mg/kg of CHLOR could rescue the enhanced acoustic startle of Fmr1-KO2 mice tested one hour afterwards. We indeed applied exactly the same experimental procedures previously used for Fmr1-KO mice to Fmr1-KO2 mice bred and maintained as previously described.

Figure 13:
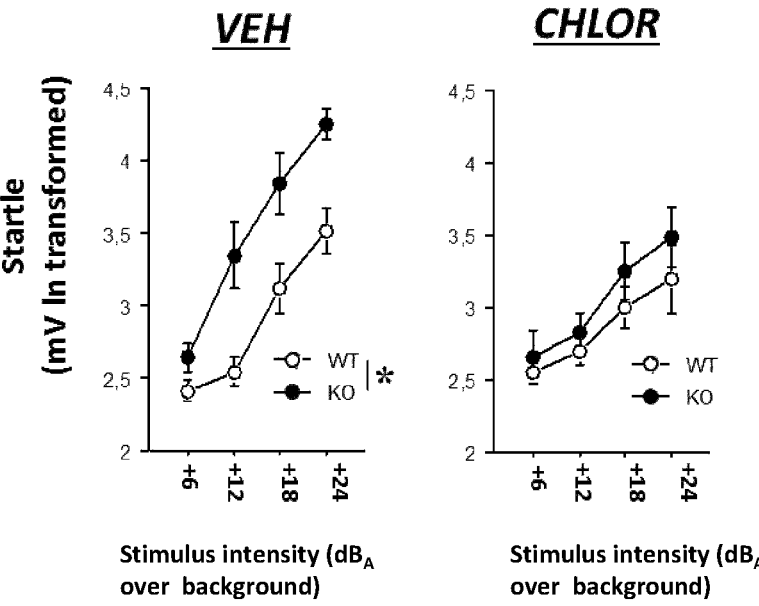
FIG. 13: shows graphs representing the acute effects of CHLOR (5 mg/kg) on the acoustic startle response in Fmr1-KO2 mice i.e., second generation Fmr1 deficient mice, and their WT littermates: n=6-8; *=p<0.05. Treatments were administered 1 h before behavioural testing. Stimulus intensities are expressed over (+) a background of 66 dB.

Acute CHLOR eliminated the exaggerated startle response of KO2 mice (FIG. 13), as previously demonstrated in the KO model of the first generation [overall effects of genotype: $F_{(1,24)}=16.07$, $p<0.001$ and treatment $F_{(1,24)}=6.14$, $p<0.05$; interaction genotype x treatment: $F_{(3,72)}=4.45$, $p<0.05$; genotype effects in separate ANOVAs: in VEH $F_{(1,11)}=38.71$, $p<0.0001$; in CHLOR, n.s.].

Conclusions

The above data demonstrated the efficacy of Chlorzoxazone in rescuing the behavioural abnormalities of Fmr1-KO mice (using models of first and second generation). The therapeutic impact of chlorzoxazone was demonstrated both in acute and chronic administration, showing higher efficacy than another molecule proposed to treat FXS, i.e., Metformin. Interestingly, the effects of our molecule were specific for the behavioural FXS-like phenotypes (no effect on macro-orchidism), suggesting that brain rather than peripheral BK channels may be preferentially targeted by our treatment. Furthermore, no aversive side effects were observed following chronic (10 days) treatments, as only a slight weight loss (2% of initial body weight) was detected (Metformin had a more pronounced effect on body weight, i.e., about 4%). Finally, although acute therapeutic effects of a lower dose (75%of the original dose of 5 mg/kg) were found on hyperactivity, the dose of 5 mg/kg seems the most appropriate to induce the most varied and robust behavioural rescue of the FXS-phenotype of Fmr1-KO mice.

Example 7: Evaluation of the Behavioural Effects of Chlorzoxazone (CHLOR) in an Animal Model of Williams-Beuren Syndrome Williams-Beuren syndrome (WBS) is a rare developmental disorder caused by the deletion of a piece of chromosome 7 (7q11.23). WBS has been only recently modeled by the CD mutant mouse having a deletion of the equivalent locus on mouse chromosome 5, resulting in a genetic defect that is very similar to the human situation. Indeed, these mice have been shown to have physical and behavioral deficits that recapitulate the symptoms seen in human patients, including cardiovascular, motor, social and sensory alterations. Here we used a novel treatment, 1a chlorzoxazone, to eliminate some major behavioural abnormalities shown by CD mice.

Example 7.1: Experimental Subjects

Subjects were adult (4-5 months old) male CD mutant mice and their wild-type litter-mates, bred in our animal facility of Bordeaux University. CD breeders, heterozygous for the CD mutation, were originally obtained from Dr. Victoria Campuzano, at the University of Pompeu Fabra, in Barcelona (Spain). Breeding trios were formed by mating two heterozygous CD males with a wild-type C57BL/6J female purchased from Janvier (Le Genest St Isle, France). After 2 weeks the sire was removed and the females were single caged and left undisturbed until weaning of the pups. Mice were weaned at 21 days of age and group-housed with their same-sex littermates (3-5/cage). On the same day, tail samples were collected for DNA extraction and subsequent PCR assessment of the genotypes as previously described (Segura-Puimedon et al., 2014). Only litters including males of both genotypes (WT and KO) were used for experiments. NMRI female mice (12±1 week old) purchased from Janvier (Le Genest St Isle, France) were used as social stimuli during the social interaction test. This strain has been selected for its high level of sociability and was previously employed in several social studies from our group on Fmr1-KO mice. Mice were group-housed (4-5/cage) and left undisturbed upon arrival at least one week before the social interaction test.

All animals were housed in polycarbonate standard cages (33×15×14 cm in size; Tecniplast, Limonest, France), provided with litter (SAFE, Augy, France) and a stainless-steel wired lid, and enriched with a cotton nestlet. Food (SAFE, Augy, France) and water were provided ad libitum. The animals were maintained in a temperature (22° C.) and humidity (55%) controlled vivarium, under a 12:12 hrs light-dark cycle (lights on at 7 a.m.). All experimental procedures were in accordance with the European Communities Council Directive of 24 Nov. 1986 (86/609/EEC) and local French legislation.

Example 7.2: Behavioural Tests

To evaluate the therapeutic potential of CHLOR we have chosen behavioural tests that have revealed altered phenotypes in CD mice based on previous data from Dr. Campuzano's team and from our pilot studies. These phenotypes include motor coordination deficits (rotarod test), hypo-activity (the open field test), hyper-sociability (the direct social interaction test for social habituation), altered daily activities/natural occurring behaviours (test for nesting abilities in a novel environment), and sensory hyper-responsiveness (acoustic startle test).

The tests have been chosen for the following crucial advantages. They allow detecting behavioural abnormalities of CD mice and most of these tests were sensitive to the therapeutic effects of the molecule CHLOR in the Fmr1-KO mouse, modeling another neurodevelopmental disorder, i.e., Fragile X syndrome). They also allow a rapid (because of the short duration and the possibility of testing multiple animals at the same time) assessment of mouse behaviour. Furthermore, they require minimal manipulation and stress of the subjects, thus allowing repeated testing of the same mice (and reducing the number of subjects needed).

All behavioral tests (except nest building) were carried out during the light phase of the cycle. Mice were habituated to the experimental room prior to all behavioral tests, being individually housed in standard polycarbonate cages provided with sawdust, food, and water bottles and left undisturbed for at least 10-15 min before testing began.

Rotarod test for motor coordination: An electrical accelerating rotarod for mice (Model 7650; Ugo Basile, Stoelting, Wood Dale, Ill.) was used. Mice were placed on the rotating drum at the baseline speed of 4 rpm. During the 5-min observation period, the speed of rotation increased linearly to 40 rpm. Mice were given three trials, with an intertrial interval of one hour. Each trial ended when the mouse fell from the apparatus or when 5 min had elapsed.

The latency to fall from the rotating drum was recorded, averaged across trials and ln-transformed to better conform to the assumptions of parametric ANOVA.

Open field test: this is one of the most widely used tests to assess locomotor activity and exploration in laboratory mice. The apparatus consisted of 4 white opaque plastic arenas (42×26×15 cm). Each mouse was placed in the center of the arena and left free to explore it for 5 minutes. Automated Tracking of the videos obtained from a camera above the open field was performed with Ethovision (version 11, Noldus Technology, Wageningen, Netherlands) to analyze the total distance traveled.

Direct social interaction test: Social interaction was assessed in a 30×15×14 cm cage, covered by a flat metal grid and with approximately 3 cm of sawdust on the floor, where male subjects were previously isolated for one hour. An unfamiliar NMRI female (3 months-old), was then introduced into the testing cage and left there for 6 min. Stimulus females were housed in unisexual groups in a female-only animal room and were in the non-oestrous phase when tested (as assessed by the analysis of vaginal smears).

Testing sessions were recorded, and videos analyzed with Observer XT (version 7, Noldus, The Netherlands). Affiliative behaviours of the male subject were evaluated, including sniffing the head and the snout of the partner, its anogenital region, or any other part of the body; allogrooming (grooming the partner) and traversing the partner's body by crawling over/under from one side to the other. Social habituation was assessed through the analysis of the time spent in affiliative behaviours across 2-min bins.

Nest-building behaviour in a novel environment: The apparatus consisted of an unfamiliar Plexiglas cage (30×15× 14 cm), covered by a flat metal grid, with approximately 3 cm of sawdust on the floor, provided with food and a water bottle. Mice were singly placed in the apparatus in the presence of nesting material (one Nestlet, 2.7 g, 2.5×2.5 cm and 5 mm thick compressed cotton; identical to the material provided in the home cage) and left undisturbed overnight. Nest building scoring was performed by a trained experimenter blinded to the genotype and treatment of the animals, using the following standardized scoring scale: 1: Nestlet not noticeably shredded; 2: Nestlet 10 to 50% shredded, not used as a nest; 3: Nestlet shredded 50 to 90%, but the shredded material remains scattered in the cage and is not used as a nest; 4: Nestlet shredded >90%, and shredded material used as a flat nest; and 5: Nestlet shredded >90% and used as a rounded nest with sides covering the mouse.

Acoustic startle test: The apparatus consisted of four acoustic startle chambers for mice (SR-LAB, San Diego Instruments, San Diego, Calif., USA). Each comprised a non-restrictive cylindrical enclosure made of clear Plexiglas attached horizontally on a mobile platform, which was in turn resting on a solid base inside a sound-attenuated isolation cubicle. A high-frequency loudspeaker mounted directly above the animal enclosure inside each cubicle produced a continuous background noise of 65/66 dBA and various acoustic stimuli in the form of white noise. Vibrations of the Plexiglas enclosure caused by the whole-body startle response of the animal were converted into analog signals by a piezoelectric unit attached to the platform. These signals were digitized and stored by a computer. The sensitivity of the stabilimeter was routinely calibrated to ensure consistency between chambers and across sessions. A session began when the animals were placed into the Plexiglas enclosure (to which they were habituated for 5 min in the absence of acoustic stimuli the day before the test, in order to minimize the stress).

We used two protocols to evaluate acoustic startle test in our CD mice. First, we performed the test with a protocol involving low intensity stimuli that has been used so far only in Fmr1-KO mice where it has allowed detecting the sensory-hyper responsiveness of these FX mice. After 5 min oh habituation, mice were presented with pulses of white sound of 20 ms duration and varying intensity: +6, +12 +18 and +24 dB over the 66 db background level (namely 72, 78, 84 and 90 dB). Each intensity was presented 8 times, in a randomized order with variable intervals (10 sec to 20 sec)

between the onset of each pulse. As the results obtained with this first procedure did not show a convincing phenotype of our mutants, another protocol was applied thus providing an extensive assessment of acoustic startle response from low (69 dB) to high (120 dB) intensities. Ten pulse intensities were used (over a background noise of 65 dB): 69, 73, 77, 81, 85, 90, 95, 100, 110 and 120 dB lasting for either 20 or 40 ms. Mice were acclimatized to the apparatus for two minutes before the first trial began. The first six trials consisted of six trials at 120 dBA, with three trials at each of the two possible stimulus durations. These trials served to stabilize the animals' startle response and were not included in the overall analysis. Subsequently, the animals were presented with 5 blocks of discrete test trials. Each block consisted of twenty pulse-alone trials, one for each intensity and duration, presented in a pseudorandom order. The inter-trials interval was variable (9-19 s) with an average duration of 14 s.

For all procedures, a total of 130 readings of the whole-body startle response were taken at 0.5-ms intervals (i.e., spanning across 65 ms), starting at the onset of the pulse stimulus. The average amplitude (in mV) over the 65 ms was used to determine the stimulus reactivity and further averaged across trials. A natural logarithmic transformation was applied in order to fulfill the normality criteria requested by parametric ANOVA.

Example 7.3: Drug Preparation

All injectable solutions were freshly prepared on each experimental day following the same procedures described before for Fmr1 mice. CHLOR was dissolved in saline solution containing 1.25% DMSO and 1.25% Tween80 and the same solution without drugs was used for the VEH control group. CHLOR was administered at the dose of 5 mg/kg in both acute and chronic studies, as this dose was the most effective in inducing therapeutic behavioural effects in Fmr1-KO mice.

Example 7.4: Statistical Analysis

All data were analyzed with ANOVA using treatment and genotype as the between-subject factors and adding trials (for the rotarod), stimulus intensity (acoustic startle), 2-min bins (social interaction) as the within-subject factors. Post-hoc comparisons were performed when a significant interaction genotype x treatment was found using Tukey's-Kramer test. Otherwise, separate one-way ANOVAs in each treatment group with genotype as the between subject factor were conducted, if appropriate. All analyzes were carried out using Statview and PASW Statistics 18.

Example 7.5: Study 1—Acute Behavioural Effects of CHLOR in CD Mice

Mice received a single i.p. injection of VEH solution or CHLOR (5 mg/kg). One hour after injection, animals were submitted to the rotarod test, the open field, the social interaction test, and acoustic startle test with low intensity stimuli.

Figure 14:
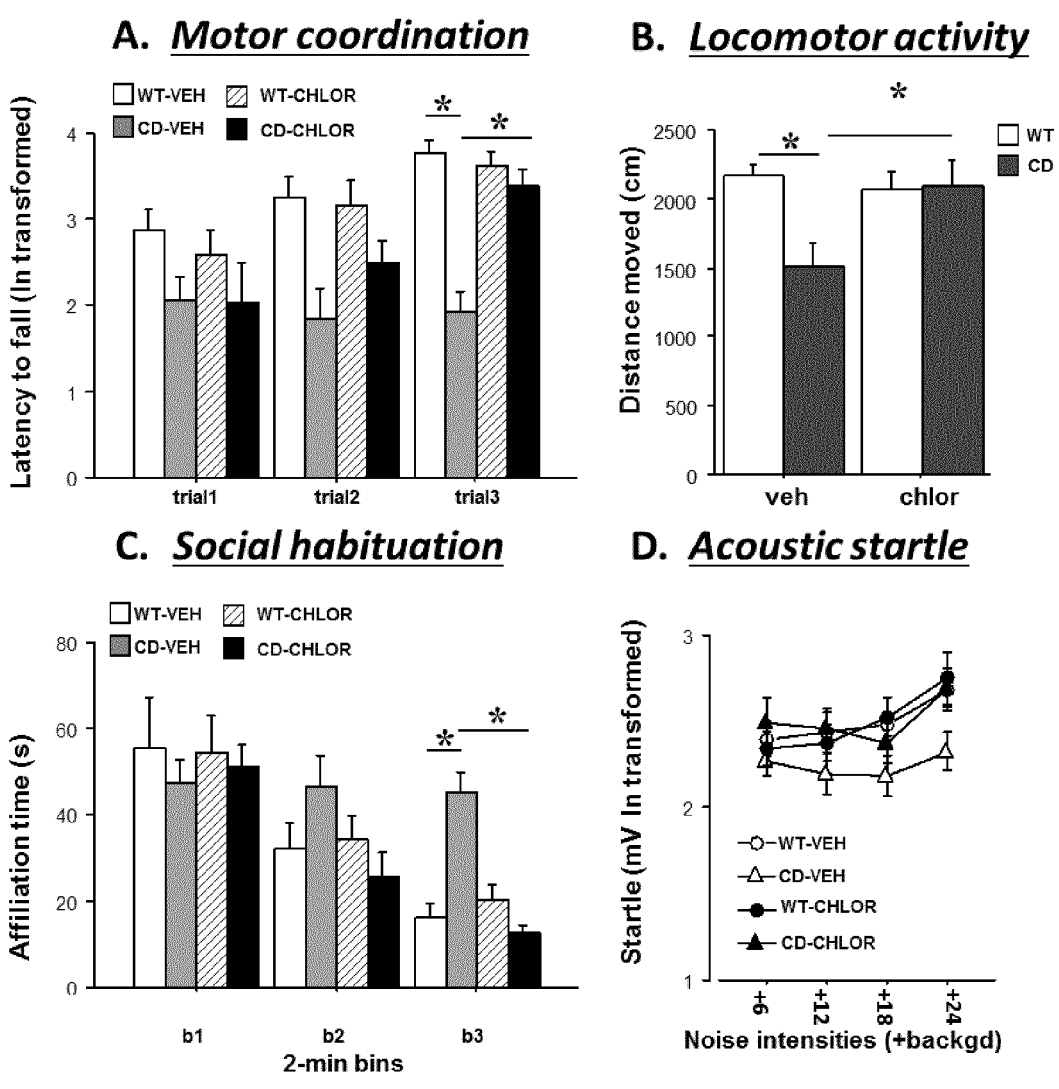
FIGS. 14A-D: are graphs showing the acute effects of chlorzoxazone (CHLOR; 5 mg/kg) in mice with Williams-Beuren complete deletion (CD) and their WT littermates: Behavioural tests were conducted 1 h after a single i.p. injection and they included rotarod test for motor coordination (A), open field test for locomotor activity (B), social habituation during direct social interaction with a WT female (C), and acoustic startle response test (D) with low intensity stimuli (background level=66 dB). n=6-14; *=p<0.05.

As expected, CD mice treated with VEH showed motor alterations, evident as an overall reduction in the latency to fall from the rotarod and hypoactivity in the open field (FIGS. 14A and 14B), and deficits in social habituation (FIG. 14C). The abnormalities in motor coordination in the rotarod test (FIG. 14A) were attenuated by acute CHLOR administration that was able to significantly improve the motor learning abilities of mutant mice on the $3^{rd}$ trial [interaction genotype x treatment: $F(1.41)=4.84$, $p<0.05$ and treatment x trial $F(2.84)=3.32$, $p<0.05$; genotype x treatment effect in separate ANOVA on trial 3: $F(1.43)=19.34$, $p<0.0001$; post-hoc: KO-VEH versus WT-VEH and versus KO-CHLOR]. Acute CHLOR fully eliminated the hypoactivity of CD mice in the open field [FIG. 14B; interaction genotype x treatment: $F(1.45)=6.31$, $p<0.01$; post-hoc: KO-VEH versus WT-VEH and versus KO-CHLOR]. CHLOR also restored social habituation in the direct social interaction test (FIG. 14C), CD mice treated with CHLOR showing a time-dependent reduction in social investigation similar to WT mice [genotype x treatment x 2-min bins: $F(2.42)=3.33$, $p<0.05$; post-hoc: KO-VEH versus WT-VEH and versus KO-CHLOR on the last time bin]. CD mice treated with VEH showed a tendency to reduce sensory responsiveness in the acoustic startle test, especially at the highest intensities (FIG. 14D). Nonetheless, this phenotypic difference did not reach statistical significance [genotype x stimulus intensity: $F(3.138)=2.29$, $p=0.08$; treatment effect and its interactions: n.s.]; hence, we employed a more extensive evaluation of acoustic startle in our subsequent study with chronic administration.

Example 7.6: Study 2—Chronic Effects of CHLOR in CD Mice

Mice received a daily i.p. injection of VEH solution or CHLOR (5 mg/kg) for 10 days, following the experimental protocol previously used in our study showing behavioural effects of chronic CHLOR in Fmr1-KO mice. Behavioural tests were carried out 24 hs after the last injection, in order to avoid acute confounding effects.

Figure 15:
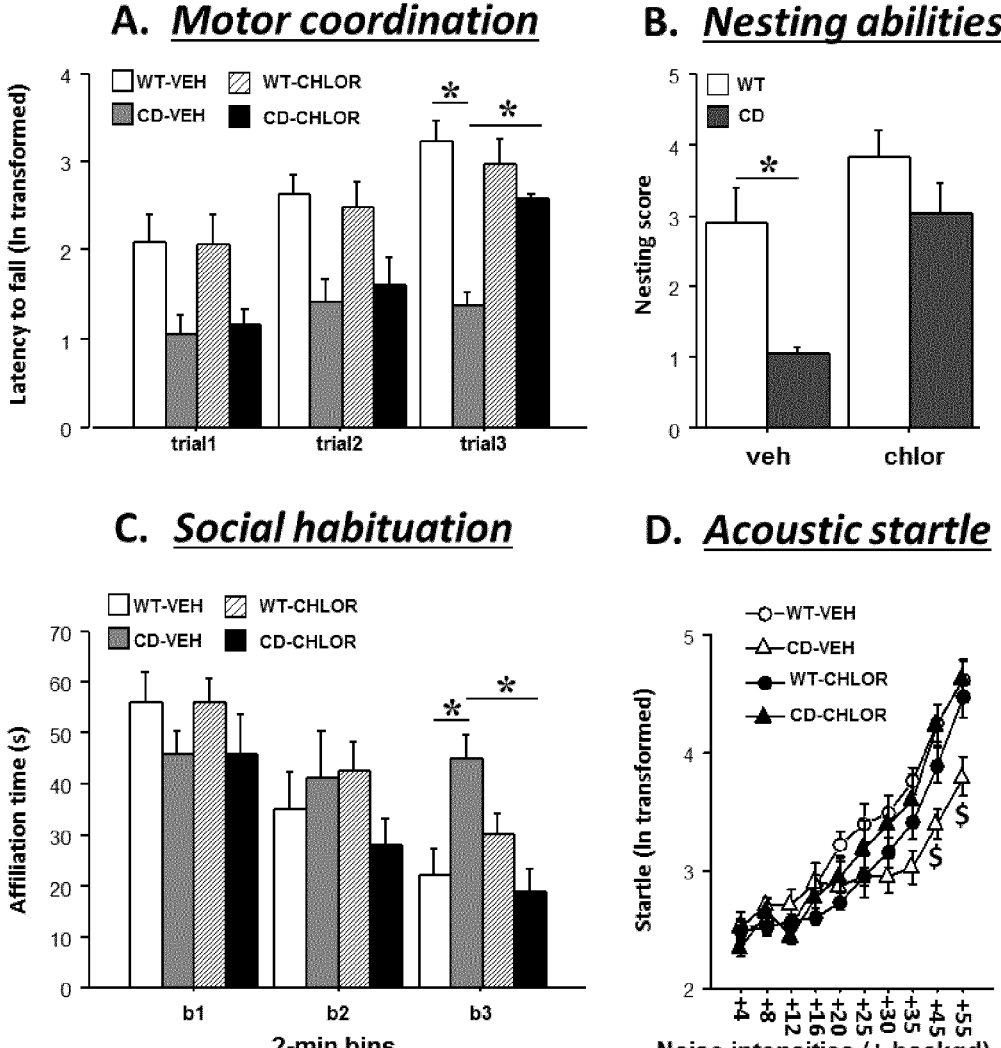
FIGS. 15A-D: are graphs showing the chronic effects of chlorzoxazone (CHLOR; 5 mg/kg) in mice with Williams- Beuren complete deletion (CD) and their WT littermates: Behavioural tests were conducted after 10 days of i.p. injections, with a 24 hs interval from the last administration. The rotarod test for motor coordination (A), nest building assessment (B), social habituation during direct social interaction with a WT female (C), and acoustic startle response test (D, background level: 65 dB). n=8-10; *=p<0.05; $=versus KO-CHLOR and WT-VEH.

As expected, CD mice treated with VEH showed deficits in motor abilities and daily activities (FIGS. 15A and B), reduced social habituation (FIG. 15C) and acoustic startle response (FIG. 15D); all these abnormalities were attenuated or rescued by acute CHLOR administration. The abnormalities of CD mice in motor coordination in the rotarod test (FIG. 15A) were attenuated by acute CHLOR administration, improving motor learning on the $3^{rd}$ trial [interaction genotype x treatment x trial: $F(2.66)=2.95$, $p=0.06$; genotype x treatment effect in separate ANOVA on trial 3: $F(1.33)=9.42$, $p<0.01$; post-hoc: KO-VEH versus WT-VEH and versus KO-CHLOR]. Acute CHLOR fully eliminated the reduced nesting abilities of CD mice [FIG. 15B; genotype and treatment effects: $F(1.34)=9.97$ and 12.49, both $p<0.01$; genotype effect from separate ANOVAs: in VEH: $F(1.15)=9.78$, $p<0.01$, in CHLOR: n.s.]. CHLOR also restored social habituation in the direct social interaction test (FIG. 15C), CD mice treated with CHLOR showing a time-dependent reduction in social investigation similar to WT mice, an habituation process that was absent in CD-VEH animals [genotype x treatment x 2-min bins: $F(2.68)=5.41$, $p<0.01$; post-hoc: KO-VEH versus WT-VEH and versus KO-CHLOR on the last time bin]. Finally, CHLOR rescued the acoustic hyporesponsiveness of CD mice that was mostly evident at the highest stimulus intensities [FIG. 15D; genotype x treatment x stimulus intensity: $F(9.306)=5.75$, $p<0.0001$; post-hoc: KO-VEH versus WT-VEH and versus KO-CHLOR on the two highest intensities].
Conclusions Above data demonstrated the efficacy of Chlorzoxazone in rescuing the behavioural abnormalities of CD mice, i.e., the last generation mouse model of WBS. The therapeutic impact of chlorzoxazone was demonstrated both in acute and chronic administration, showing efficacy also outside the acute time window. Our data therefore suggest that plasticity long-term mechanisms, e.g., rescue of dendritic spine abnormalities, may be triggered by chronic stimulation of BK channels induced by CHLOR. As the effective dose used in these studies was the same previously showing therapeutic effects on the behaviour of the Fmr1-KO mouse model for FXS, our findings strongly supported the hypothesis that CHLOR may correct pathological mechanisms common to multiple neurodevelopmental pathologies.

The invention claimed is:

1. A method of treating neuropsychiatric pathologies in a subject, wherein the neuropsychiatric pathologies consist of Fragile X Syndrome (FXS), Angelman syndrome, Williams-Beuren syndrome, hyperacusis, Smiths-Magenis syndrome, Prader-Willi syndrome, 7q11.23 duplication syndrome, or cri-du-chat syndrome, wherein the method comprises administering to the subject a therapeutically effective amount of a composition comprising an agonist of the large-conductance calcium-activated potassium channel (BKCa channel), and wherein the agonist is chlorzoxazone or acetazolamide.

2. The method of claim 1, wherein said agonist of the large-conductance calcium-activated potassium channel (BKCa channel) is also an agonist of the small-conductance calcium-activated potassium channel (SK channel).

3. The method of claim 1, wherein said neuropsychiatric pathologies present similar symptoms including cognitive disorder, behavioral disorder, and sensory hyperexcitability.

4. The method of claim 3, wherein administering the therapeutically effective amount of the compound of claim 1 reduces the severity of at least one of the symptoms.

5. The method of claim 3, wherein administering the therapeutically effective amount of the compound of claim 1 additionally reduces neuropsychiatric pathologies and/or symptoms including trembling, epilepsy and neuropathic pains.

6. The method of claim 1, wherein said therapeutic amount of the compound of formula (I) is in the range of 500 mg/day to 3 g/day with a frequency ranging from 2 to 4 times per day.

7. The method of claim 1, wherein said therapeutic amount is around 750 mg/day, 1.5 g/day, 2.25 g/day, or 3 g/day at a frequency of 3 or 4 times per day.

8. The method of claim 1, wherein said neuropsychiatric pathologies are Fragile X Syndrome (FXS), Williams-Beuren syndrome, and/or hyperacusis.

9. The method of claim 8, wherein the severity of one or more symptoms of FXS is cognitive disorder, behavioral disorder, or sensory hyperexcitability which is alleviated, reduced or eliminated in said subject.

10. The method of claim 9, wherein further symptoms of FXS include:
(i) mental retardation with learning difficulties and reading delays, (ii) behavioral disorders including irritability, anxiety, attention deficit, hyperactive behaviors, and autism spectrum disorders (ASDs), (iii) heightened sensitivity to sensory stimuli, such as tactile irritation, audiogenic seizures, tinnitus, and nystagmus, or (iv) dyskinesia, tremor activity, and one or more of said symptoms are alleviated or reduced in said subject.

11. The method according to claim 1, comprising administering a further medication selected from antipsychotics, antidepressants, mood-stabilizers, anticonvulsants or antiepileptics, anxiolytics, and psychostimulants.

12. The method according to claim 1, comprising administering a subject in need thereof a therapeutically effective amount of at least one drug, wherein said at least one drug is fenobam, AFQ056, OVI0I, STX209, acamprosate, ZYN002, MG01ICI, arbaclofen, minocycline, or a combination of minocycline lovastatin, sertraline, BPN14770, ganaxolone, STX107, RO4917523, NNZ-2566, dietary supplement SXF-TRA152, AZD7325, ampakine, or CX516.

13. The method according to claim 1, further comprising administering said composition in a pharmaceutically acceptable carrier.

14. The method of claim 3, wherein the sensory hyper-excitability comprises an increased sensitivity to ranges of sound intensity levels and/or ranges of frequencies.

\* \* \* \* \*